United States Patent
Cosenza et al.

(10) Patent No.: US 6,656,973 B2
(45) Date of Patent: Dec. 2, 2003

(54) (E)-4-CARBOXYSTYRL-4-CHLOROBENZYL SULFONE AND PHARMACEUTICAL COMPOSITIONS THEREOF

(75) Inventors: Stephen C. Cosenza, Voorhees, NJ (US); M. V. Ramana Reddy, Upper Darby, PA (US); E. Premkumar Reddy, Villanova, PA (US)

(73) Assignee: Temple University - Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 10/305,694

(22) Filed: Nov. 27, 2002

(65) Prior Publication Data

US 2003/0149109 A1 Aug. 7, 2003

Related U.S. Application Data

(63) Continuation of application No. 09/689,281, filed on Oct. 11, 2000.
(60) Provisional application No. 60/159,123, filed on Oct. 12, 1999.

(51) Int. Cl.[7] .............................................. A61K 31/10
(52) U.S. Cl. ..................................................... 514/710
(58) Field of Search ........................................ 514/710

(56) References Cited

U.S. PATENT DOCUMENTS

| | | | |
|---|---|---|---|
| 2,532,612 A | 12/1950 | Doumani | 260/609 |
| 3,185,743 A | 5/1965 | Combe et al. | 260/682 |
| 3,418,101 A | 12/1968 | Buchholtz et al. | 71/72 |
| 3,514,386 A | 5/1970 | Oswald et al. | 204/162 |
| 3,917,714 A | 11/1975 | Richmond | 260/607 A |
| 4,161,407 A | 7/1979 | Campbell | 96/114 |
| 4,386,221 A | 5/1983 | Hyatt et al. | 568/28 |
| 4,937,388 A | 6/1990 | Bushell et al. | 568/56 |
| 5,659,087 A | 8/1997 | Aikins et al. | 568/27 |

FOREIGN PATENT DOCUMENTS

| | | |
|---|---|---|
| WO | WO99/18068 | 4/1999 |

OTHER PUBLICATIONS

D. Bhaskar Reddy, N.S. Reddy, S. Reddy, M.V.R. Reddy and S. Balasubramanyam, Org. Prep. Proc. Int., 20(3):205–212 (1988).
D. Bhasker Reddy, P. V. Ramana Reddy, V. Padmavathi, and M.V.R. Reddy, Sulfur Lett., 13(2):83–90 (1991).
M.V.R. Reddy and S. Reddy, Acta Chim. Acad. Sci. Hung., 115(3):269–271 (1984).
M.V.R. Reddy, V. Vijayalakshmi, D. Bhaskar Reddy and P.V. Ramana Reddy, Phosphorus, Sulfur Silicon Relat. Elem., 60:209–214 (1991).
M.V. Reddy and S. Reddy, Acta Chim Acad. Sci. Hung., 120(4):275–280 (1985).
M.V.R. Reddy and S. Reddy, Synthesis No. 4, 322–323 (1984).
M.V.R. Reddy, S. Reddy and D.B. Reddy, Sulfur Lett., 7(2):43–48 (1987).
Reddy et al., "A New Route for the Synthesis of Styrylbenzylsulfones, Precursors of 1–Benzylsulfonyl–2–Arylcyclopropanes", Phosphorus, Sulfur, and Silicon, 53:285–290 (1990).
Mieczyslaw Makosza and Irina Krylova, "Some Reactions of the Chloromethyl trans–beta–Styryl Sulfone Carbanion", Liebigs Ann./Recueil, pp. 2337–2340 (1997).

(List continued on next page.)

Primary Examiner—Russell Travers
Assistant Examiner—Mojdeh Bahar
(74) Attorney, Agent, or Firm—Drinker Biddle & Reath LLP

(57) ABSTRACT

Provided are the compound (E)-4-carboxystyryl-4-chlorobenzyl sulfone, pharmaceutically acceptable salts thereof, and pharmaceutical compositions thereof.

2 Claims, 6 Drawing Sheets

OTHER PUBLICATIONS

Reddy et al., "Phase Transfer Catalysis—A Facile Method For Cyclopropanation Of Some Isomeric Styryl Sulfone Carbanion", *Liebigs Ann./Recueil*, pp. 2337–2340 (1997).

CA:124:175763, abs of Reddy et al., *Indian J. Heterocycl. Chem.*, (May 1995), 5 (1), 11–14.

CA:124: 146025, Abstract Only of Reddy et al., *Indian J. Heterocycl. Chem.* (1995), 4(4), 259–264.

CA:126: 166162, Thompson et al. Abstract Only of *Cancer Res.*, (Feb. 1997) 57(2), 267–271.

Benati, et al., *J. Org. Chem.*, 59:2818–2823 (1994).

CA:120: 323356 Abstract Only of Reddy et al., *Sulf. Lett.* (1993), 16(5–6), 227–35.

CA:122: 132682 Abstract Only of Reddy et al., *Phosphorus, Sulfur Silicon Relat. Elem.* (1994), 90(1–4), 1–10.

CA:124: 8731 Abstract Only of Reddy et al., *Indian J. Chem. Sect. B: Org. Chem. Incl. Med. Chem.* (1995) 34B(9), 816–22.

CA: 76: 121420 Abstract Only of Findlay et al. *Brit J. Dermatol., Supp.* (1971), No. 7, 44–9.

CA:105: 133446 abs of Naidu et al. *Proc.—Indian Acad. Sci., Chem. Sci* (1985), 95(4), 391–5.

CA:126: 185889 abs of Japanese Pat. App. 09–03,037 (Jan. 7, 1997).

Griggs, J. J., Embase Abstract, AN:1998287056, 1998.

(E)-4-CARBOXYSTYRL-4-CHLOROBENZYL SULFONE AND PHARMACEUTICAL COMPOSITIONS THEREOF

CROSS-REFERENCE TO RELATED APPLICATION

This application is a continuation of Ser. No. 09/689,281 filed Oct. 11, 2000 now pending, which claims the benefit of the filing date of U.S. provisional patent application Ser. No. 60/159,123, filed Oct. 12, 1999, is hereby claimed pursuant to 35 U.S.C. 119(e), and the entire disclosure thereof is incorporated herein by reference.

FIELD OF THE INVENTION

The invention relates to the field of anticancer chemotherapy, and cytoprotective agents administered before, during or after anticancer chemotherapy to protect the normal cells of the patient from the cytotoxic effects of anticancer chemotherapeutics.

BACKGROUND OF THE INVENTION

Experimental chemotherapy has been the mainstay of treatment offered to patients diagnosed with surgically unresectable advanced cancers, or cancers refractory to standard chemotherapy and radiation therapy. Of the more effective classes of drugs, curative properties are still limited. This is because of their relatively narrow therapeutic index, restricted dosage, delayed treatments and a relatively large proportion of only partial tumor reductions. This state is usually followed by recurrence, increased tumor burden, and drug resistant tumors.

Several cytoprotective agents have been proposed to enhance the therapeutic index of anticancer drugs. For methotrexate toxicity, such agents include asparaginase, leucovorum factor, thymidine, and carbipeptidase. Because of the extensive use of anthracyclines, specific and non-specific cytoprotective agents have been proposed which have varying degrees of efficacy; included are corticosteroids, desrazoxane and staurosporin. The latter is of interest in that it includes a G1/S restriction blockade in normal cells. (Chen et al., *Proc AACR* 39:4436A, 1998).

Cisplatin is widely used and has a small therapeutic index which has spurred investigation and search of cytoprotectants. Among the cytoprotectants for cisplatin with clinical potential are mesna, glutathione, Na-thiosulfate, and amifostine (Griggs, *Leuk. Res.* 22 Suppl 1:S27–33, 1998; List et al., *Semin. Oncol.* 23(4 Suppl 8):58–63, 1996; Taylor et al., *Eur. J. Cancer* 33(10):1693–8, 1997). None of these or other proposed cytoprotectants such as oxonic acid for fluoropyrimidine toxicity, or prosaptide for paclitaxel PC12 cell toxicity, appears to function by a mechanism which renders normal replicating cells into a quiescent state.

What is needed are cytoprotective agents which are effective in protecting animals, inclusive of humans, from the cytotoxic side effects of chemotherapeutic agents.

Unrelated to the foregoing, styryl sulfones having pharmaceutical utility as anticancer agents have been reported in WO/99/18068, the entire disclosure of which is incorporated herein by reference. The compounds inhibit tumor cell growth by inducing tumor cell death without killing normal cells. The styryl sulfones are effective in a broad range of tumor types. Without wishing to be bound by any theory, it is believed that the styryl sulfones affect the Mitogen Activated Protein Kinase (MAPK) signal transduction pathway, thereby affecting tumor cell growth and viability.

SUMMARY OF THE INVENTION

It is an object of the invention to provide compositions and methods for protecting animals, inclusive of humans, from the cytotoxic side effects of chemotherapeutic agents, particularly mitotic phase cell cycle inhibitors and topoisomerase inhibitors, used in the treatment of cancer and other proliferative disorders.

It is an object of the invention provide a method for treating cancer or other proliferative disorder which reduces or eliminates cytotoxic effects on normal cells.

It is an object of the invention to enhance the effects of chemotherapeutic agents, particularly mitotic phase cell cycle inhibitors and topoisomerase inhibitors, used for the treatment of cancer or other proliferative disorders.

It is an object of the present invention to provide a therapeutic program for treating cancer or other proliferative disorder which includes administration of a cytoprotective compound prior to administration of a chemotherapeutic agent, which cytoprotective compound induces a reversible cycling quiescent state in non-tumored tissues.

It is an object of the invention to provide a method for safely increasing the dosage of chemotherapeutic agents, particularly mitotic phase cell cycle inhibitors and topoisomerase inhibitors, used in the treatment of cancer and other proliferative disorders.

According to the present invention, a method for protecting an animal from cytotoxic side effects of the administration of a mitotic phase cell cycle inhibitor or a topoisomerase inhibitor comprises administering to the animal, in advance of administration of the aforesaid inhibitor, an effective amount of at least one cytoprotective α,β unsaturated aryl sulfone compound. The term "animal" is meant to embrace human beings, as well as non-human animals.

By "α,β unsaturated aryl sulfone compound" as used herein is meant a chemical compound containing one or more α,β unsaturated aryl sulfone groups:

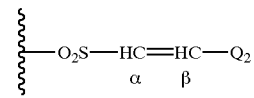

wherein $Q_2$ is substituted or unsubstituted aryl, and the hydrogen atoms attached to the α and β carbons are optionally replaced by other chemical groups.

By "substituted" means that an atom or group of atoms has replaced hydrogen as the substituent attached to a ring atom. The degree of substitution in a ring system may be mono-, di-, tri- or higher substitution.

The term "aryl", alone or in combination, means a carbocyclic aromatic system containing one, two, or more rings wherein such rings may be attached together in a pendent manner or may be fused. The term "aryl" is intended to include not only aromatic systems containing only carbon ring atoms but also systems containing one or more non-carbon atoms as ring atoms. Such systems may be known as "heteroaryl" systems. The term "aryl" is thus deemed to include "heteroaryl". Heteroaryl groups include, for example, pyridyl, thienyl, furyl, thiazolyl, pyrrolyl, and thienyl-1,1-dioxide The heterocyclic radical may be substituted or unsubstituted. The term "aryl" is not limited to ring systems with six members.

According to one embodiment, the α,β unsaturated aryl sulfone group is a styryl sulfone group:

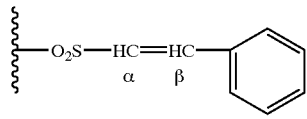

wherein the hydrogen atoms attached to the α and β carbons are optionally replaced by other chemical groups, and the phenyl ring is optionally substituted.

By "styryl sulfone" or "styryl sulfone compound" or "styryl sulfone therapeutic" as used herein is meant a chemical compound containing one or more such styryl sulfone groups.

According to another embodiment of the invention, a method of treating an individual for cancer or other proliferative disorder is provided. The method comprises administering to the animal an effective amount of at least one mitotic phase cell cycle inhibitor or topoisomerase inhibitor, and administering before the inhibitor, an effective amount of at least one cytoprotective α,β unsaturated aryl sulfone compound.

By "effective amount" of the mitotic phase cell cycle inhibitor or topoisomerase inhibitor is meant an amount of said inhibitor effective in killing or reducing the proliferation of cancer cells in a host animal. By "effective amount" of the cytoprotective α,β unsaturated aryl sulfone compound is meant an amount of compound effective to reduce the toxicity of the mitotic phase cell cycle inhibitor or topoisomerase inhibitor on normal cells of the animal.

The α,β unsaturated aryl sulfone cytoprotective compounds are characterized by cis-trans isomerism resulting from the presence of a double bond. Stearic relations around a double bond are designated as "Z" or "E". Both configurations are included in the scope of "α,β unsaturated aryl sulfone":

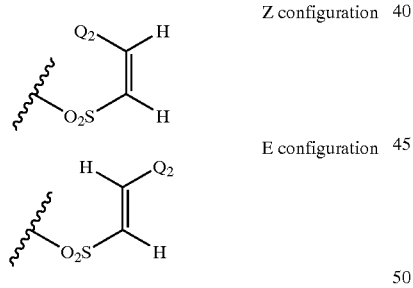

According to one embodiment, the α,β unsaturated aryl sulfone compound is a compound of the formula I:

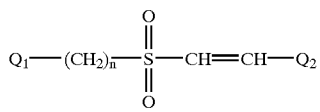

wherein:

n is one or zero;

$Q_1$ and $Q_2$ are, same or different, are substituted or unsubstituted aryl.

Preferably, n in formula I is one, that is, the compounds comprise α,β unsaturated benzylsulfones, e.g. styryl benzylsulfones.

According to one sub-embodiment, n is preferably one and:

$Q_1$ is selected from the group consisting of substituted and unsubstituted phenyl, 1-naphthyl, 2-naphthyl, 9-anthryl and an aromatic radical of formula II:

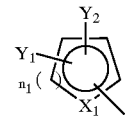

wherein
$n_1$ is 1 or 2,
$Y_1$ and $Y_2$ are independently selected from the group consisting of hydrogen, halogen, and nitro, and
$X_1$ is selected from the group consisting of oxygen, nitrogen, sulfur and

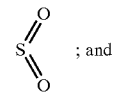

; and $Q_2$ is selected from the group consisting of substituted and unsubstituted phenyl, 1-naphthyl, 2-naphthyl, 9-anthryl and an aromatic radical of formula III:

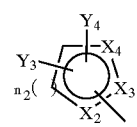

wherein
$n_2$ is 1 or 2,
$Y_3$ and $Y_4$ are independently selected from the group consisting of hydrogen, halogen, and nitro, and
$X_2$, $X_3$ and $X_4$ are independently selected from the group consisting of carbon, oxygen, nitrogen, sulfur and

provided that not all of $X_2$, $X_3$ and $X_4$ may be carbon.

According to one preferred embodiment according to formula 1, $Q_1$ and $Q_2$ are selected from substituted and unsubstituted phenyl.

Preferred compounds where $Q_1$ and $Q_2$ are selected from substituted and unsubstituted phenyl comprise compounds of the formula IV:

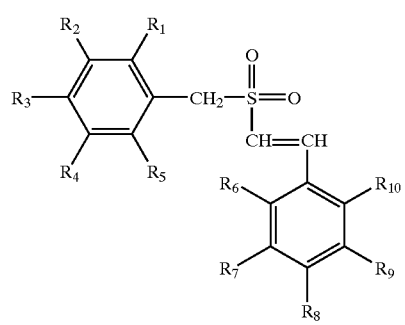

wherein:
$R_1$ through $R_{10}$ are independently selected from the group consisting of hydrogen, halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6 trifluoroalkoxy and trifluoromethyl.

In one embodiment, compounds of formula IV are at least di-substituted on at least one ring, that is, at least two of $R_1$ through $R_5$ and/or at least two of $R_5$ through $R_{10}$, are other than hydrogen. In another embodiment, compounds of formula IV are at least trisubstituted on at least one ring, that is, at least three of $R_1$ through $R_5$ and/or at least three of $R_5$ through $R_{10}$, are other than hydrogen.

In one embodiment, the cytoprotective compound has the formula V:

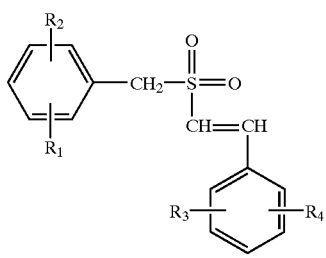

V wherein $R_1$, $R_2$, $R_3$ and $R_4$ are independently selected from the group consisting of hydrogen, halogen, C1–C8 alkyl, C1–C8 alkoxy, nitro, cyano, carboxy, hydroxy and trifluoromethyl.

According to a particularly preferred embodiment of the invention, the cytoprotective compound is according to formula V, and $R_1$ and $R_2$ are independently selected from the group consisting of hydrogen, chlorine, fluorine, bromine, cyano, and trifluoromethyl; and $R_3$ and $R_4$ are independently selected from the group consisting of hydrogen, chlorine, fluorine and bromine.

Preferred compounds according to formula V having the E-configuration include, but are not limited to, (E)-4-fluorostyryl-4-chlorobenzylsulfone; (E)4-chlorostyryl-4-chlorobenzylsulfone; (E)-2-chloro-4-fluorostyryl-4-chlorobenzylsulfone; (E)-4-carboxystyryl-4-chlorobenzyl sulfone; (E)-4-fluorostyryl-2,4-dichlorobenzylsulfone; (E)-4-fluorostyryl-4-bromobenzylsulfone; (E)-4-chlorostyryl-4-bromobenzylsulfone; (E)-4-bromostyryl-4-chlorobenzylsulfone; (E)-4-fluorostyryl-4-trifluoromethylbenzylsulfone; (E)-4-fluorostyryl-3,4-dichlorobenzylsulfone; (E)-4-fluorostyryl-4-cyanobenzylsulfone; (E)-2,4-dichloro-4-chlorobenzylsulfone; and (E)-4-chlorostyryl-2,4-dichlorobenzylsulfone.

According to another embodiment, compounds of formula I have the Z configuration wherein $R_1$ and $R_3$ are hydrogen, and $R_2$ and $R_4$ are selected from the group consisting of 4-Cl, 4-F and 4-Br. Such compounds include, for example, (Z)-4-chlorostyryl-4-chlorobenzylsulfone; (Z)-4-chlorostyryl-4-fluorobenzylsulfone; (Z)-4-fluorostyryl-4-chlorobenzylsulfone; (Z)-4-bromostyryl-4-chlorobenzylsulfone; and (Z)-4-bromostyryl-4-fluorobenzylsulfone.

According to another embodiment, the cytoprotective α,β unsaturated aryl sulfone compound is a compound of the formula VI:

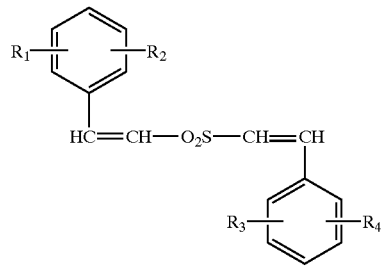

VI wherein $R_1$, $R_2$, $R_3$, and $R_4$ are independently selected from the group consisting of hydrogen, halogen, C1–8 alkyl, C1–8 alkoxy, nitro, cyano, carboxyl, hydroxyl, and trifluoromethyl.

In one embodiment, $R_1$ in formula VI is selected from the group consisting of hydrogen, chlorine, fluorine and bromine; and $R_2$, $R_3$ and $R_4$ are hydrogen.

According to yet another embodiment, the cytoprotective α,β unsaturated aryl sulfone compound is a compound of the formula VII:

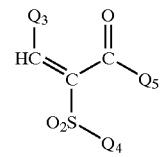

VII wherein $Q_3$, $Q_4$ and $Q_5$ are independently selected from the group consisting of phenyl and mono-, di-, tri-, tetra- and penta-substituted phenyl where the substituents, which may be the same or different, are independently selected from the group consisting of halogen, C1–C8 alkyl, C1–C8 alkoxy, nitro, cyano, carboxy, hydroxy, phosphonato, amino, sulfamyl, acetoxy, dimethylamino(C2–C6 alkoxy), C1–C6trifluoroalkoxy and trifluoromethyl.

According to one sub-embodiment of formula VII, the cytoprotective α,β unsaturated aryl sulfone compound is a compound of the formula VIIa:

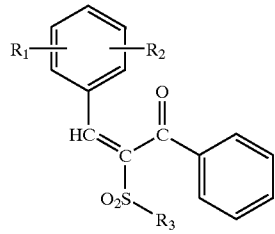

VIIa wherein $R_1$ and $R_2$ are independently selected from the group consisting of hydrogen, halogen, C1–C8 alkyl, C1–8 alkoxy, nitro, cyano, carboxyl, hydroxyl, and trifluoromethyl; and $R_3$ is selected from the group consisting of unsubstituted phenyl, mono-substituted phenyl and di-substituted phenyl, the substituents on the phenyl ring being independently selected from the group consisting of halogen and C1–8 alkyl.

Preferably, $R_1$ in formula VIIa is selected from the group consisting of fluorine and bromine; $R_2$ is hydrogen; and $R_3$ is selected from the group consisting of 2-chlorophenyl, 4-chlorophenyl, 4-fluorophenyl, and 2-nitrophenyl.

A preferred cytoprotective styryl sulfone according to formula VIIa is the compound wherein $R_1$ is fluorine, $R_2$ is hydrogen and $R_3$ is phenyl, that is, the compound 2-(phenylsulfonyl)-1-phenyl-3-(4-fluorophenyl)-2-propen-1-one.

By "dimethylamino(C2–C6 alkoxy)" is meant $(CH_3)_2N(CH_2)_nO$— wherein n is from 2 to 6. Preferably, n is 2 or 3. Most preferably, n is 2, that is, the group is the dimethylaminoethoxy group, that is, $(CH_3)_2NCH_2CH_2O$—.

By "phosphonato" is meant the group $—PO(OH)_2$.

By "sulfamyl" is meant the group $—SO_2NH_2$.

Where a substituent on an aryl nucleus is an alkoxy group, the carbon chain may be branched or straight, with straight being preferred. Preferably, the alkoxy groups comprise C1–C6 alkoxy, more preferably C1–C4 alkoxy, most preferably methoxy.

DETAILED DESCRIPTION OF THE INVENTION

Figure 1:
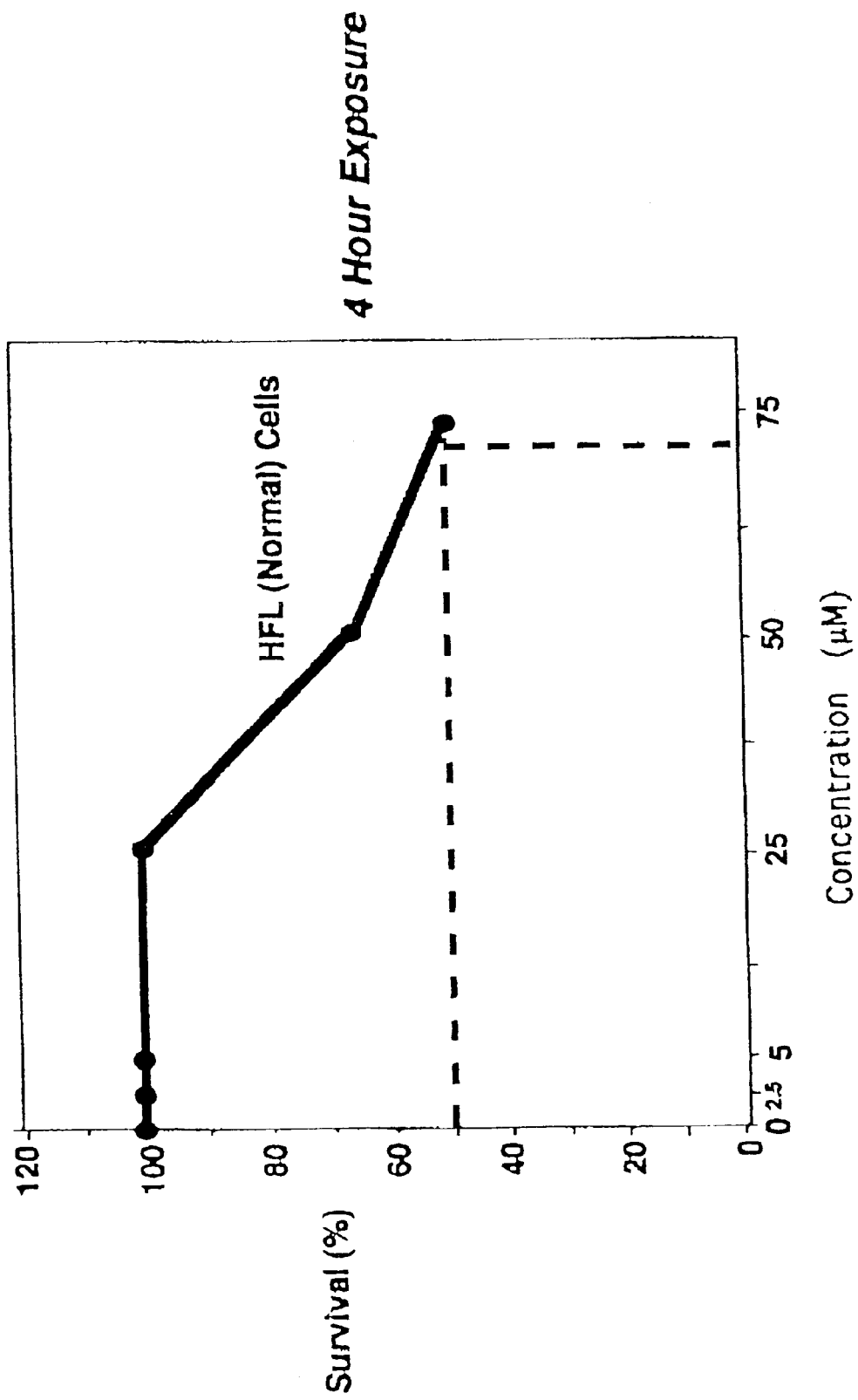
FIG. 1 shows the plating efficiency of normal human fibroblasts (HFL-1) treated with various concentrations of the styryl sulfone (E)-4-fluorostyryl-4-chlorobenzylsulfone. The cells were incubated with the indicated concentration of the styryl sulfone for 24 hours, washed three times and harvested by trypsinization. Cells were plated at various dilutions to determine colony-forming ability.

According to the present invention, certain $\alpha,\beta$ unsaturated aryl sulfones are administered with the aim of reducing or eliminating adverse effects of anticancer treatment with chemotherapeutic agents which comprise mitotic phase cell cycle inhibitors.

The usual description of the cell cycle describes the cycle in terms of a series of phases—interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, S and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

By "mitotic phase cell cycle inhibitor" is meant a chemical agent whose mechanism of action includes inhibition of a cell's passage through any portion of the mitotic (M) phase of the cell cycle. Such agents include, by way of example and not limitation, taxanes, such as paclitaxel and its analogs; vinca alkaloids such as vincristine and vinblastine; colchicine; estramustine; and naturally occurring macrolides such as rhizoxin, maytansine, ansamitocin P-3, phomopsin A, dolastatin 10 and halichrondin B.

Paclitaxel is an anti-mitotic drug presently used as an initial treatment for ovarian, breast and lung cancer, with moderate success. Vincristine is a well-established anti-mitotic drug widely used for the treatment of breast cancer, Hodgkin's lymphoma and childhood cancers.

The topoisomerases constitute a group of enzymes that catalyze the conversion of DNA from one topological form to another by introducing transient breaks in one or both strands of a DNA duplex. Topological isomers are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA. By "topoisomerase inhibitor" is meant a chemical agent whose mechanism of action includes interfering with the function of a topoisomerase.

Inhibitors of topoisomerase I include, for example, adriamycin and etoposide. Inhibitors of topoisomerase II include, for example, camptothecin, irinotecan and topotecan.

The $\alpha,\beta$ unsaturated aryl sulfones differ from other known cytoprotective agents in that they not only protect normal cells, but are also operationally cytotoxic in tumor cells. In normal cells, the $\alpha,\beta$ unsaturated aryl sulfones induce a reversible resting state rendering the normal cells relatively refractory to the cytotoxic effect of mitotic phase cell cycle inhibitors and topoisomerase inhibitors. Data indicating the cytotoxic effect of the $\alpha,\beta$ unsaturated aryl sulfone compounds on tumor cells is set forth in PCT/US/98/20580; PCT/US00/08565; and in the following commonly assigned U.S. patent applications Ser. Nos.: 60/127,683, filed Apr. 2, 1999; 60/143,975, filed Jul. 15, 1999; 09/282,855, filed Mar.

31, 1999; and 60/197,368, filed Apr. 14, 2000. The entire disclosures of the aforesaid PCT and U.S. patent applications are incorporated herein by reference. It is believed that the α,β unsaturated aryl sulfones, and particularly the styryl sulfones, are the first compounds which are both cytoprotective in normal cells and toxic in cancer cells.

As demonstrated herein, normal human fibroblasts exposed to α,β unsaturated aryl sulfones in vitro exhibit transiently reduced replication rates. When the same cells are then exposed to a mitotic phase cell cycle inhibitor such as paclitaxel, the cells are protected from the toxic effects of the inhibitor. Simultaneous exposure of α,β unsaturated aryl sulfone and the inhibitor does not result in protection. The precise cytoprotective mechanism of action of the α,β unsaturated aryl sulfones on normal tissues is unknown. However, based on experimental models, and without wishing to be bound by any theory, these compounds may affect several elements in normal cells inducing a reversible quiescent cell-cycling state in which transit through mitosis, and many of the changes necessary for such passage, are down regulated, inactivated or absent. Tumor cells appear to be refractory to this effect of the α,β unsaturated aryl sulfones and in fact continue cycling with readily activated programmed cell death pathways. According to other possible mechanisms of protection, anticancer agent-induced proinflammatory cytokine release from monocytes or macrophages, activation of JNK-1 death pathway induction, and P34Cdc2 kinase may be rendered innocuous by pre-exposure to α,β unsaturated aryl sulfones.

In tumored cells, α,β unsaturated aryl sulfones exhibit contrasting characteristics. They are cytotocidal at a low concentration rather than being reversible cytostatic, even at high concentrations. The α,β unsaturated aryl sulfones impact on normal cells is to cause a transitory cycling arrest. Paclitaxel cytotoxic effects include proinflammatory cytokine release of IL-1, TNF, and nitric oxide (Kirikae et al. *Biochem Biophys Res Commun.* 245:698–704, 1998; White et al. *Cancer Immunol. Immunoth.* 46:104–112, 1998). Its major effect is mitotic blockade, and induction of c-Jun NHα-terminal kinase/AP-1 death pathways. (Lee et al., *J. Biol Chem* 273:28253–28260, 1998; Amato et al., *Cancer Res.* 58:241–247, 1998). As cytoprotective agents against the toxicity of paclitaxel, the α,β unsaturated aryl sulfones presumably also induce a direct or indirect biochemical blockade of macrophage/monocyte response to paclitaxel in normal cells, and interfere with the cell death signaling pathway.

The schedule of administration of the cytotoxic drug, i.e., mitotic phase cell cycle inhibitor or topoisomerase inhibitor, can be any schedule with the stipulation that α,β unsaturated aryl sulfone is administered prior to the cytotoxic drug. The sulfone should be administered far enough in advance of the cytotoxic drug such that the former is able to reach the normal cells of the patient in sufficient concentration to exert a cytoprotective effect on the normal cells. In one embodiment, the sulfone is administered at least about 4 hours before administration of the cytotoxic drug. The sulfone may be administered as much as about 48 hours, preferably no more than about 36 hours, prior to administration of the cytotoxic drug. Most preferably, the sulfone is administered about 24 hours before the cytotoxic drug. The sulfone may be administered more or less than 24 hours before the cytotoxic effect, but the protective effect of the α,β unsaturated aryl sulfones is greatest when administered about 24 hours before the cytotoxic drug. One or more cytotoxic drugs may be administered. Similarly, one or more α,β unsaturated aryl sulfones may be combined.

Where the cytotoxic drug or drugs is administered in serial fashion, it may prove practical to intercalate sulfones within the schedule with the caveat that a 4–48 hour period, preferably a 12–36 hour period, most preferably a 24 hour period, separates administration of the two drug types. This strategy will yield partial to complete eradication of cytotoxic drug side effects without affecting anticancer activity.

For example, the mitotic inhibitor may be given daily, or every fourth day, or every twenty-first day. The sulfone may be given 24 hours previous to each round of inhibitor administration, both as a cytoprotective agent and as an antitumor agent.

It may be appreciated that by "administered" is meant the act of making drug available to the patient such that a physiological effect is realized. Thus, contemplated within the scope of the present invention is the instillation of drug in the body of the patient in a controlled or delayed release formulation, with systemic or local release of the drug to occur at a later time. Thus, a depot of sulfone maybe administered to the patient more than 48 hours before the administration of cytotoxic drug provided that at least a portion of the sulfone is retained in the depot and not released until the 48 hour window prior to the administration of the cytotoxic drug.

The α,β unsaturated aryl sulfone compound may be administered by any route which is sufficient to bring about the desired cytoprotective effect in the patient. Routes of administration include enteral, such as oral; and parenteral, such as intravenous, intraarterial, intramuscular, intranasal, rectal, intraperitoneal, subcutaneous and topical routes.

The α,β unsaturated aryl sulfone may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the α,β unsaturated aryl sulfone may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of α,β unsaturated aryl sulfone to obtain the cytoprotective benefit will, of course, be determined by the particular circumstances of the individual patient including, the size, weight, age and sex of the patient, the nature and stage of the disease, the aggressiveness of the disease, and the route of administration, and the cytotoxicity of the mitotic phase cell cycle inhibitor. For example, a daily dosage of from about 0.01 to about 150 mg/kg/day may be utilized, more preferably from about 0.05 to about 50 mg/kg/day. Higher or lower doses are also contemplated.

The dosage, formulation, route and schedule of administration of the mitotic phase cell cycle inhibitor is carried out according to the known protocols for the drug. It should be pointed out, however, that a more aggressive form of treatment, i.e. delivery of a higher dosage, is contemplated according to the present invention due to the protection of the normal cells afforded by the α,β unsaturated aryl sulfones. Thus the cytoprotective effect of the sulfone may permit the physician in some circumstances to increase the dosage of the mitotic phase cell cycle inhibitor above levels presently recommended.

While the sulfone and the mitotic phase cell cycle inhibitor may be administered by different routes, the same route of administration is preferred.

The α,β unsaturated aryl sulfones may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, galactaric and galacturonic acid. Suitable pharmaceutically acceptable base addition salts include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding α,β unsaturated aryl sulfone by reacting, for example, the appropriate acid or base with the sulfone compound.

The α,β unsaturated aryl sulfones are characterized by cis-trans isomerism resulting from the presence of one or more double bonds. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p.127–138. Stearic relations around a double bond are designated as "Z" or "E".

(E)-α,β unsaturated aryl sulfones may be prepared by Knoevenagel condensation of aromatic aldehydes with benzylsulfonyl acetic acids or arylsulfonyl acetic acids. The procedure is described by Reddy et a., *Acta. Chim. Hung.* 115:269–71 (1984); Reddy et al., *Sulfur Letters* 13:83–90 (1991); Reddy et al., *Synthesis* No. 4, 322–23 (1984); and Reddy et al., *Sulfur Letters* 7:43–48 (1987), the entire disclosures of which are incorporated herein by reference.

According to the Scheme 1 below, $R_a$ and $R_b$ each represent from zero to five substituents on the depicted aromatic nucleus. For purposes of illustration, and not limitation, the aryl groups are represented as phenyl groups, that is, the synthesis is exemplified by the preparation of styryl benzylsulfones. Accordingly, the benzyl thioacetic acid B is formed by the reaction of sodium thioglycollate and a benzyl chloride A. The benzyl thioacetic acid B is then oxidized with 30% hydrogen peroxide to give a corresponding benzylsulfonyl acetic acid C. Condensation of the benzylsulfonyl acetic acid C with an aromatic aldehyde D via a Knoevenagel reaction in the presence of benzylamine and glacial acetic acid yields the desired (E)-styryl benzylsulfone E.

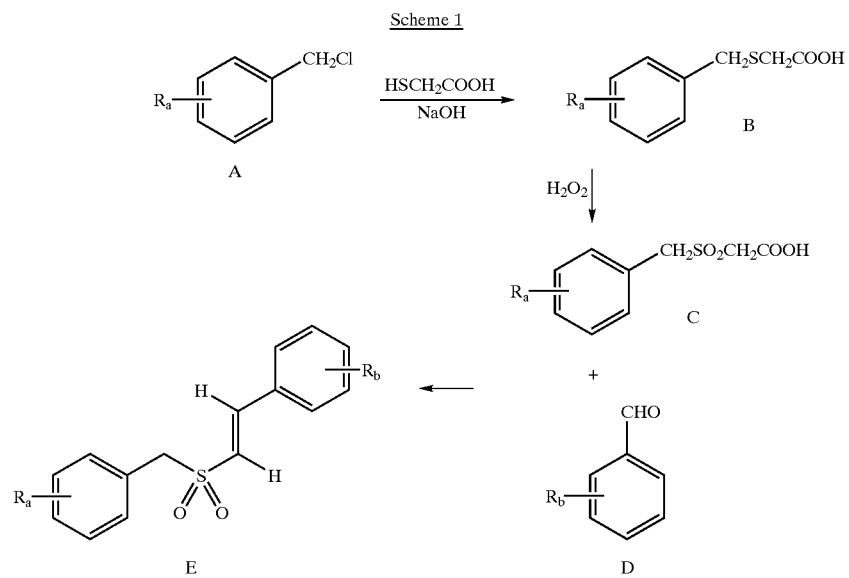

The following is a more detailed two-part synthesis procedure for preparing. (E)-styryl benzylsulfones according to the above scheme.

General Procedure 1

Synthesis (E)-Styryl Benzylsulfones

Part A. To a solution of (8 g, 0.2 mol) sodium hydroxide in methanol (200 ml), thioglycollic acid (0.1 mol) is added slowly and the precipitate formed is dissolved by stirring the contents of the flask. Then an appropriately substituted benzyl chloride (0.1 mol) is added stepwise and the reaction mixture is refluxed for 2–3 hours. The cooled contents are poured onto crushed ice and neutralized with dilute hydrochloric acid (200 ml). The resulting corresponding benzylthioacetic acid (0.1 mol) is subjected to oxidation with 30% hydrogen peroxide (0.12 mol) in glacial acetic acid (125 ml) by refluxing for 1 hour. The contents are cooled and poured onto crushed ice. The separated solid is recrystalized from hot water to give the corresponding pure benzylsulfonylacetic acid.

Part B. A mixture of the benzylsulfonyl acetic acid (10 mmol), an appropriately substituted aromatic aldehyde (10 mmol), and benzylamine (200 ml) in glacial acetic acid (12 ml) is refluxed for 2–3 hours. The contents are cooled and treated with cold ether (50 ml). Any product precipitated out is separated by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields styryl benzylsulfones as a solid material.

According to an alternative to Part A, the appropriate benzylsulfonylacetic acids may be generated by substituting a thioglycollate $HSCH_2COOR$ for thioglycollic acid, where R is an alkyl group, typically C1–C6 alkyl. This leads to the formation of the alkylbenzylthioacetate intermediate (F),

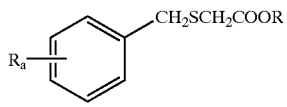

which is then converted to the corresponding benzyl thioacetic acid B by alkaline or acid hydrolysis.

(E)-styryl phenyl sulfones (formula I: n=zero; $Q_1$, $Q_2$=substituted or unsubstituted phenyl) are prepared according to the method of General Procedure 1, replacing the benzylsulfonyl acetic acid in Part B with the appropriate substituted or unsubstituted phenylsulfonyl acetic acid.

(Z)-Styryl benzylsulfones are prepared by the nucleophilic addition of the appropriate thiols to substituted phenylacetylene with subsequent oxidation of the resulting sulfide by hydrogen peroxide to yield the (Z)-styryl benzylsulfone. The procedure is generally described by Reddy et al., *Sulfur Letters* 13:83–90 (1991), the entire disclosure of which is incorporated herein as a reference.

In the first step of the (Z)-styryl benzylsulfones synthesis, the sodium salt of benzyl mercaptan or the appropriate substituted benzyl mercaptan is allowed to react with phenylacetylene or the appropriate substituted phenylacetylene forming the pure (Z)-isomer of the corresponding styryl benzylsulfide in good yield.

In the second step of the synthesis, the (Z)-styryl benzylsulfide intermediate is oxidized to the corresponding sulfone in the pure (Z)-isomeric form by treatment with hydrogen peroxide.

The following is a more detailed two-part synthesis procedure for preparing (Z)-styryl benzylsulfones:

Procedure 2

Synthesis of (Z)-Styryl Benzylsulfones

Part A. To a refluxing methanolic solution of substituted or unsubstituted sodium benzylthiolate prepared from 460 mg (0.02 g atom) of (i) sodium, (ii) substituted or unsubstituted benzyl mercaptan (0.02 mol) and (iii) 80 ml of absolute methanol, is added freshly distilled substituted or unsubstituted phenylacetylene. The mixture is refluxed for 20 hours, cooled and then poured on crushed ice. The crude product is filtered, dried and recrystalized from methanol or aqueous methanol to yield a pure (Z)-styryl benzylsulfide.

Part B. An ice cold solution of the (Z)-styryl benzylsulfide (3.0 g) in 30 ml of glacial acetic acid is treated with 7.5 ml of 30% hydrogen peroxide. The reaction mixture is refluxed for 1 hour and then poured on crushed ice. The separated solid is filtered, dried, and recrystalized from 2-propanol to yield the pure (Z)-styryl benzylsulfone. The purity of the compounds is ascertained by thin layer chromatography and geometrical configuration is assigned by analysis of infrared and nuclear magnetic resonance spectral data.

The bis(styryl) sulfones of formula VI are prepared according to Procedure 3:

Procedure 3

Synthesis of (E)(E)- and (E)(Z)-bis(Styryl) Sulfones

To freshly distilled phenyl acetylene (51.07 g, 0.5 mol) is added sodium thioglycollate prepared from thioglycollic acid (46 g, 0.5 mol) and sodium hydroxide (40 g, 1 mol) in methanol (250 ml). The mixture is refluxed for 24 hours and poured onto crushed ice (500 ml) after cooling. The styrylthioacetic acid, formed after neutralization with dilute hydrochloric acid (250 ml), is filtered and dried; yield 88 g (90%); m.p. 84–86° C.

The styrylthioacetic acid is then oxidized to styrylsulfonylacetic acid as follows. A mixture of styrylthioacetic acid (5 g, 25 mmol) in glacial acetic acid (35 ml) and 30% hydrogen peroxide (15 ml) is heated under reflux for 60 minutes and the mixture is poured onto crushed ice (200 ml) after cooling. The compound separated is filtered and recrystalized from hot water to give white crystalline flakes of (Z)-styrylsulfonylacetic acid; yield 2.4 g (41%); m.p. 150–51° C.

A solution of (Z)-styrylsulfonylacetic acid (2.263 g, 10 m mol) in glacial acetic acid (6 ml) is mixed with an aromatic aldehyde (10 mmol) and benzylamine (0.2 ml) and refluxed for 3 hours. The reaction mixture is cooled, treated with dry ether (50 ml), and any product separated is collected by filtration. The filtrate is diluted with more ether and washed successively with a saturated solution of sodium hydrogen carbonate (15 ml), sodium bisulfite (15 ml), dilute hydrochloric acid (20 ml) and finally with water (30 ml). Evaporation of the dried ethereal layer yields (E)(Z)-bis(styryl) sulfones.

(E),(E)-bis(styryl)sulfones are prepared following the same procedure as described above with exception that sulfonyldiacetic acid is used in place of (Z)-styrylsulfonylacetic acid, and twice the amount of aromatic aldehyde (20 mmol) is used.

The styryl sulfones of formula VII, which are systematically identified as 2-(phenylsulfonyl)-1-phenyl-3-phenyll-2- propen-1-ones, may be prepared according to either Method A or Method B of Procedure 4:

Procedure 4

Synthesis of 2-(Phenylsulfonyl)-1-phenyl-3-phenyl-2-propen-1-ones

These compounds are synthesized by two methods which employ different reaction conditions, solvents and catalysts.

Method A: Phenacyl aryl sulfones are made by refluxing α-bromoacetophenones (0.05 mol) and sodium arylsulfinates (0.05 mol) in absolute ethanol (200 ml) for 6–8 hours. The product which separates on cooling is filtered and washed several times with water to remove sodium bromide. The product is then recrystalized from ethanol: phenacyl-phenyl sulfone, m.p. 90–91° C.; phenacyl-p-fluorophenyl sulfone, m.p. 148–149° C.; phenacyl-p-bromophenyl sulfone, m.p. 121–122° C.; phenacyl-p-methoxy-phenyl sulfone, m.p. 104–105° C.; p-nitrophenacyl-phenyl sulfone, m.p. 136–137° C.

A solution of phenacyl aryl sulfone (0.01 mol) in acetic acid (10 ml) is mixed with an araldehyde (0.01 mol) and benzylamine (0.02 ml) and refluxed for 3 hours. The solution is cooled and dry ether (50 ml) is added. The ethereal solution is washed successively with dilute hydrochloric acid, aqueous 10% NaOH, saturated NaHSO3 solution and water. Evaporation of the dried ethereal layer gives a solid product which is purified by recrystallization.

Method B: Dry tetrahydrofuran (200 ml) is taken in a 500 ml conical flask flushed with nitrogen. To this, a solution of titanium (IV) chloride (11 ml, 0.01 mol) in absolute carbon tetrachloride is added dropwise with continuous stirring. The contents of the flask are maintained at −20° C. throughout the course of the addition. A mixture of phenacyl aryl sulfone (0.01 mol) and aromatic aldehyde (0.01 mol) is added to the reaction mixture and pyridine (4 ml, 0.04 mol) in tetrahydrofuran (8 ml) is added slowly over a period of 1 hour. The contents are stirred for 10–12 hours, treated with water (50 ml) and then ether (50 ml) is added. The ethereal layer is separated and washed with 15 ml of saturated solutions of 10% sodium hydroxide, sodium bisulfite and brine. The evaporation of the dried ethereal layer yields 2-(phenylsulfonyl)-1-phenyl-3-phenyl-2 propen-1-ones.

The practice of the invention is illustrated by the following non-limiting examples. The synthesis of various α,β unsaturated aryl sulfone active agents, for use as cytoprotective agents according to the practice of the invention, is set forth as "Synthesis Examples". Other material is contained in "Examples".

Synthesis Example 1
(E)-styryl phenyl sulfone
A solution of phenyl sulfonylacetic acid (0.01 mol) and benzaldehyde (0.01 mol) was subjected to the Procedure 1, Part B. The title compound was obtained in 68–72% yield.

Synthesis Example 2
(E)-4-chlorostyryl phenyl sulfone
A solution of phenyl sulfonylacetic acid (0.01 mol) and 4-chlorobenzaldehyde (0.01 mol) was subjected to Procedure 1, Part B. The title compound was obtained in 78–80% yield.

Synthesis Example 3
(E)-2,4-dichlorostyryl phenyl sulfone
A solution of phenyl sulfonylacetic acid (0.01 mol) and 2,4-dichlorobenzaldehyde (0.01 mol) was subjected to Procedure 1, Part B. The title compound was obtained in 60–65% yield.

Synthesis Example 4
(E)-4-bromostyryl phenyl sulfone
A solution of phenyl sulfonylacetic acid (0.01 mol) and 4-bromobenzaldehyde (0.01 mol) was subjected to Procedure 1, Part B. The title compound was obtained in 78–80% yield.

Synthesis Example 5
(E)-4-chlorostyryl 4-chlorophenyl sulfone
A solution of 4-chlorophenyl sulfonylacetic acid (0.01 mol) and 4-chlorobenzaldehyde (0.01 mol) was subjected to Procedure 1, Part B. The title compound was obtained in 70–72% yield.

Synthesis Example 6
(E)-4-methylstyryl 4-chlorophenyl sulfone
A solution of 4-chlorophenyl sulfonylacetic acid (0.01 mol) and 4-methylbenzaldehyde (0.01 mol) was subjected to Procedure 1, Part B. The title compound was obtained in 60–64% yield.

Synthesis Example 7
(E)4-methoxystyryl 4-chlorophenyl sulfone
A solution of 4-chlorophenyl sulfonylacetic acid (0.01 mol) and 4-methoxybenzaldehyde (0.01 mol) was subjected to Procedure 1, Part B. The title compound was obtained in 68–70% yield.

Synthesis Example 8
(E)-4-bromostyryl 4-chlorophenyl sulfone
A solution of 4-chlorophenyl sulfonylacetic acid (0.01 mol) and 4-bromobenzaldehyde (0.01 mol) was subjected to Procedure 1, Part B. The title compound was obtained in 80% yield.

Synthesis Example 9
(E)-2-chlorostyryl benzyl sulfone
A solution of benzyl sulfonylacetic acid (0.01 mol) and 2-chlorobenzaldehyde (0.01 mol) was subjected to Procedure 1, Part B. The title compound was obtained in 72% yield.

Synthesis Example 10
E-4-chlorostyryl benzyl sulfone
A solution of benzyl sulfonylacetic acid (0.01 mol) and 4-chlorobenzaldehyde (0.01 mol) was subjected to Procedure 1, Part B. The title compound was obtained in 78% yield.

Synthesis Example 11
E-4-fluorostyryl 4-chlorobenzyl sulfone
A solution of 4-chlorobenzyl sulfonylacetic acid (0.01 mol) and 4-fluorobenzaldehyde (0.01 mol) was subjected to Procedure 1, Part B. The title compound was obtained in 72% yield.

Synthesis Example 12
(E)-4-chlorostyryl 4-chlorobenzyl sulfone
A solution of 4-chlorobenzyl sulfonylacetic acid (0.01 mol) and 4-chlorobenzaldehyde (0.01 mol) was subjected to Procedure 1, Part B. The title compound was obtained in 80% yield.

Synthesis Example 13
(E)-4-fluorostyryl 4-fluorobenzyl sulfone
A solution of 4-fluorobenzyl sulfonylacetic acid (0.01 mol) and 4-fluorobenzaldehyde (0.01 mol) was subjected to Procedure 1, Part B. The title compound was obtained in 73% yield.

Synthesis Example 14
(E)-2,4-difluorostyryl 4-fluorobenzyl sulfone

A solution of 4-fluorobenzyl sulfonylacetic acid (0.01 mol) and 2,4-difluorobenzaldehyde (0.01 mol) was subjected to Procedure 1, Part B. The title compound was obtained in 68% yield.

Synthesis Example 15
(E)4-fluorostyryl 4-bromobenzyl sulfone

A solution of 4-bromobenzyl sulfonylacetic acid (0.01 mol) and 4-fluorobenzaldehyde (0.01 mol) was subjected to Procedure 1, Part B. The title compound was obtained in 82% yield.

Synthesis Example 16
(E)-4-bromostyryl 4-bromobenzyl sulfone

A solution of 4-bromobenzyl sulfonylacetic acid (0.01 mol) and 4-bromobenzaldehyde (0.01 mol) was subjected to Procedure 1, Part B. The title compound was obtained in 88% yield.

Synthesis Example 17
(E)-4-bromostyryl 4-fluorobenzyl sulfone

A solution of 4-fluorobenzyl sulfonylacetic acid (0.01 mol) and 4-bromobenzaldehyde (0.01 mol) was subjected to Procedure 1, Part B. The title compound was obtained in 82% yield.

Synthesis Example 18
(E)-4-chlorostyryl 4-bromobenzyl sulfone

A solution of 4-bromobenzylsulfonyl acetic acid (0.01 mol) and 4-chlorobenzaldehyde (0.01 mol) was subjected to Procedure 1, Part B. The title compound was obtained in 88% yield.

Synthesis Example 19
(E)-4-bromostyryl 4-chlorobenzyl sulfone

A solution of 4-chlorobenzylsulfonyl acetic acid (0.01 mol) and 4-bromobenzaldehyde (0.01 mol) was subjected to Procedure 1, Part B. The title compound was obtained in 92% yield.

Infrared and nuclear magnetic resonance spectroscopy analyses of the compounds of Synthesis Examples 1 through 19 are set forth in Table 1:

TABLE 1

IR and NMR Spectroscopy

| Syn. Ex. | IR (KR pellet) vC=C | vSO$_2$ | NMR (CDCl$_3$) (δ ppm) |
|---|---|---|---|
| 1 | 1638 | 1380, 1140 | 6.81(1H, d, J$_{H,H}$=15.6), 7.2–7.8(m, 10H), 7.49(1H, d) |
| 2 | 1627 | 1368, 1155 | 6.88(1H, d, J$_{H,H}$=15.2), 7.15–7.9(m, 9h), 7.54(1H, d) |
| 3 | 1635 | 1370, 1140 | 6.92(1H, d, J$_{H,H}$=15.6), 7.3–7.85(m, 9H), 7.62(1H, d) |
| 4 | 1642 | 1355, 1142 | 6.90(1H, d, J$_{H,H}$=15.4), 7.25–7.9(m, 9H), 7.58(1H, d) |
| 5 | 1645 | 1328, 1126 | 6.86(1H, d, J$_{H,H}$=15.6), 7.30–7.75(m, 8H), 7.55(1H, d) |
| 6 | 1650 | 1344, 1116 | 2.45(3H, s), 6.83(1H, d, J$_{H,H}$=15.8), 7.25–7.85(m, 8H), 7.48(1H, d) |
| 7 | 1658 | 1320, 1128 | 3.85(3H, s), 6.85(1H, d, J$_{H,H}$=15.4), 7.28–7.82(m, 8H), 7.60(1H, d) |
| 8 | 1660 | 1311, 1148 | 6.84(1H, d, J$_{H,H}$=15.6), 7.25–7.8(m, 8H), 7.60(1H, d) |
| 9 | 1638 | 1318, 1140 | 4.30(2H, s), 6.81(1H, d, J$_{H,H}$=15.6), 7.30–7.75(m, 9H), 7.58(1H) |
| 10 | 1642 | 1312, 1140 | 4.34(2H, s), 6.78(1H, d, J$_{H,H}$=15.7), 7.26–7.85(m, 9H), 7.54(1H) |
| 11 | 1650 | 1305, 1150 | 4.32(2H, s), 6.82(1H, d, J$_{H,H}$=16.0), 7.22–7.76(m, 8H), 7.52(1H) |
| 12 | 1658 | 1316, 1132 | 4.38(2H, s)6.86(1H, d, J$_{H,H}$=16.2), 7.26–7.85(m, 8H), 7.58(1H) |
| 13 | 1640 | 1307, 1132 | 4.44(2H, s), 6.84(1H, d, J$_{H,H}$=15.8), 7.20–7.78(m, 8H), 7.58(1H) |
| 14 | 1646 | 1326, 1145 | 4.40(2H, s), 6.88(1H, d, J$_{H,H}$=15.6), 7.33–7.72(m, 7H), 7.58(1H) |
| 15 | 1660 | 1330, 1144 | 4.46(2H, s), 6.90(1H, d, J$_{H,H}$=16.2), 7.24–7.78(m, 8H), 7.58(1H) |
| 16 | 1658 | 1316, 1132 | 4.38(2H, s), 6.76(1H, d, J$_{H,H}$=16.3), 7.36–7.84(m, 8H), 7.58(1H) |
| 17 | 1644 | 1314, 1152 | 4.43(2H, s), 6.84(1H, d, J$_{H,H}$=15.8), 7.28–7.76(m, 8H), 7.60(1H) |
| 18 | 1652 | 1321, 1148 | 4.42(2H, s), 6.78(1H, d, J$_{H,H}$=16.0), 7.34–7.80(m, 8H), 7.54(1H) |
| 19 | 1638 | 1330, 1138 | 4.38(2H, s), 6.82(1H, d, J$_{H,H}$=15.6), 7.28–7.78(m, 8H), 7.55(1H) |

Synthesis Example 20
(E)-4-Fluorostyryl-4-trifluoromethylbenzylsulfone

A solution of 4-trifluoromethylbenzylsulfonylacetic acid (10 mmol) and 4-fluorobenzaldehyde (10mmol) was subjected to the Procedure 1, Part B. The title compound melting point 166–168° C., was obtained in 82% yield.

Synthesis Example 21
(E)-4-Chlorostyryl-4-trifluoromethylbenzylsulfone

A solution of 4-trifluoromethylbenzylsulfonylacetic acid (10 mmol) and 4-chlorobenzaldehyde (10 mmol) was subjected to the Procedure 1, Part B. The title compound, melting point 164–168° C., was obtained in 88% yield.

Synthesis Example 22
(E)-4-Bromostyryl-4-trifluoromethylbenzylsulfone

A solution of 4-trifluoromethylbenzylsulfonylacetic acid (10 mmol) and 4-bromobenzaldehyde (10 mmol) was subjected to the Procedure 1, Part B. The title compound, melting point 181–183° C., was obtained in 85% yield.

Synthesis Example 23
(E)-4-Fluorostyryl-2,4-dichlorobenzylsulfone

A solution of 2,4-dichlorobenzylsulfonyl acid (10 mmol) and 4-fluorobenzaldehyde (10 mmol) was subjected to the Procedure 1, Part B. The title compound, melting point 146–148° C., was obtained in 78% yield.

Synthesis Example 24
(E)-4-Chlorostyryl-2,4-dichlorobenzylsulfone

A solution of 2,4-dichlorobenzylsulfonylacetic acid (10 mmol) and 4-chlorobenzaldehyde (10 mmol) was subjected to the Procedure 1, Part B. The title compound, melting point 148–149° C., was obtained in 84% yield.

Synthesis Example 25
(E)-4-Fluorostyryl-3,4-dichlorobenzylsulfone

A solution of 3,4-dichlorobenzylsulfonylacetic acid (10 mmol) and 4-fluorobenzaldehyde (10 mmol) was subjected to the Procedure 1, Part B. The title compound, melting point 120–122° C., was obtained in 82% yield.

Synthesis Example 26
(E)-4-Chlorostyryl-3,4-dichlorobenzylsulfone

A solution of 3,4-dichlorobenzylsulfonylacetic acid (10 mmol) and 4-chlorobenzaldehyde (10 mmol) was subjected to the Procedure 1, Part B. The title compound, melting point 149–151° C., was obtained in 86% yield.

Synthesis Example 27
(E)-4-Bromostyryl-3,4-dichlorobenzylsulfone

A solution of 3,4-dichlorobenzylsulfonylacetic acid (10 mmol) and 4-bromobenzaldehyde (10 mmol) was subjected to the Procedure 1, Part B. The title compound, melting point 154–155° C., was obtained in 84% yield.

Synthesis Example 28
(E)-4-Bromostyryl-4-nitrobenzylsulfone

A solution of 4-nitrobenzylsulfonylacetic acid (10 mmol) and 4-bromobenzaldehyde (10 mmol) was subjected to the Procedure 1, Part B. The title compound, melting point 160–161° C., was obtained in 76% yield.

Synthesis Example 29
(E)-4-Fluorostyryl-4-cyanobenzylsulfone

A solution of 4-cyanobenzylsulfonylacetic acid (10 mmol) and 4-fluorobenzaldehyde (10 mmol) was subjected to the Procedure 1 Part B. The title compound, melting point 150–151° C., was obtained in 82% yield.

Synthesis Example 30
(E)-4-Chlorostyryl-4-cyanobenzylsulfone

A solution of 4-cyanobenzylsulfonyl acetic acid (10 mmol) and 4-chlorobenzaldehyde (10 mmol) was subjected to the Procedure 1, Part B. The title compound, melting point 173–177° C., was obtained in 86% yield.

Synthesis Example 31
(E)4-Bromostyryl-4cyanobenzylsulfone

A solution of 4-cyanobenzylsulfonyl acetic acid (10 mmol) and 4-bromobenzaldehyde (10 mmol) was subjected to the Procedure 1, Part B. The title compound, melting point 183–184° C., was obtained in 77% yield.

Synthesis Example 32
(E)-3,4-Difluorostyryl-4-chlorobenzylsulfone

A solution of 4-chlorobenzylsulfonyl acetic acid (10 mmol) and 3,4 difluorobenzaldehyde was subjected to the Procedure 1, Part B. The title compound, melting point 204–205° C., was obtained in 73% yield.

Synthesis Example 33
(E)-3-Chloro-4-fluorostyryl-4-chlorobenzylsulfone

A solution of 4-chlorobenzylsulfonylacetic acid (10 mmol) and 3-chloro-4-fluorobenzaldehyde was subjected to the Procedure 1, Part B. The title compound, melting point 181–183° C., was obtained in 78% yield.

Synthesis Example 34
(E)-2-Chloro-4-fluorostyryl-4-chlorobenzylsulfone

A solution of 4-chlorobenzylsulfonylacetic acid (10 mmol) and 2-chloro-4-fluorobenzaldehyde was subjected to the Procedure 1, Part B. The title compound, melting point 149–150° C., was obtained in 68% yield.

Synthesis Example 35
(E)-2,4-Dichlorostyryl-4-chlorobenzylsulfone

A solution of 4-chlorobenzylsulfonyl acetic acid (10 mmol) and 2,4-dichlorobenzaldehyde was subjected to the Procedure 1, Part B. The title compound, melting point 164–165° C., was obtained in 78% yield.

Synthesis Example 36
(E)-3,4-Dichlorostyryl-4-chlorobenzylsulfone

A solution of 4-chlorobenzylsulfonyl acetic acid (10 mmol) and 3,4 dichlorobenzaldehyde (10 mmol) was subjected to the Procedure 1, Part B. The title compound, melting point 170–171° C., was obtained in 73% yield.

Synthesis Example 37
(E)-2,3-Dichlorostyryl-4-chlorobenzylsulfone

A solution of 4-chlorobenzylsulfonyl acetic acid (10 mmol) and 2,3-dichlorobenzaldehyde (10 mmol was subjected to the Procedure 1, part B. The title compound, melting point 170–171° C., was obtained in 72% yield.

Synthesis Example 38
(Z)-styryl benzylsulfone

A solution of phenylacetylene (0.02 mol) and benzyl mercaptan (0.02 mol) and metallic sodium (0.02 g atom) was subjected to the Procedure 2, part A, to form (Z)-styryl benzylsulfide. The title compound was obtained in 65% yield by oxidation of the sulfide according to the Procedure 2, part B. $^1$HNMR (CDCl$_3$) δ4.50 (2H, s),6.65(1H, d, $J_{H,H}$=11.2),7.18–7.74 (10H aromatic+1H ethylenic).

Synthesis Example 39
(Z)-styryl 4-chlorobenzylsulfone

A solution of phenylacetylene (0.02 mol) and 4-chlorobenzyl mercaptan (0.02 mol) and metallic sodium (0.02 g atom) was subjected to Procedure 2 to form (Z)-styryl 4-chlorobenzylsulfide. The title compound was obtained in 72% yield following oxidation. $^1$HNMR (CDCl$_3$) δ4.56 (2H, s), 6.68 (1H, d, $J_{H,H}$=11.8), 7.20–7.64 (9H aromatic+1H ethylenic).

Synthesis Example 40
(Z)-styryl 2-chlorobenzylsulfone

A solution of phenylacetylene (0.02 mol) and 2-chlorobenzyl mercaptan (0.02 mol) and metallic sodium (0.02 g atom) was subjected to Procedure 2 to form (Z)-styryl 2-chlorobenzylsulfide. The title compound was obtained in 68% yield following oxidation. $^1$HNMR (CDCl$_3$) δ4.50 (2H, s), 6.65 (1H, d, $J_{H,H}$=12.0), 7.18–7.74 (9H aromatic+1H ethylenic).

Synthesis Example 41
(Z)-styryl 4-fluorobenzylsulfone

A solution of phenylacetylene (0.02 mol) and 4-fluorobenzyl mercaptan (0.02 mol) and metallic sodium (0.02 g atom) was subjected to Procedure 2 to from (Z)-styryl 4-fluorobenzylsulfide. The title compound was obtained in 70% yield following oxidation. $^1$HNMR (CDCl$_3$) δ4.58 (2H, s),6.62 (1H, d, $J_{H,H}$=11.86), 7.18–7.60 (9H aromatic+1H ethylenic).

Synthesis Example 42
(Z)-4-chlorostyryl benzylsulfone

A solution of 4-chlorophenylacetylene (0.02 mol) and benzyl mercaptan (0.02 mol) and metallic sodium (0.02 g atom) was subjected to Procedure 2 to form (Z)-4-chlorostyryl benzylsulfide. The title compound was obtained in 74% yield following oxidation. $^1$HNMR (CDCl$_3$) δ4.55 (2H, s), 6.66 (1H, d, $J_{H,H}$=12.12), 7.16–7.65 (9H aromatic+1H ethylenic).

Synthesis Example 43
(Z)-4-chlorostyryl 4-chlorobenzylsulfone

A solution of 4-chlorophenylacetylene (0.02 mol) and 4-chlorobenzyl mercaptan (0.02 mol) and metallic sodium (0.02 g atom) was subjected to Procedure 2 to form (Z)-4-chlorostyryl 4-chlorobenzylsulfide. The title compound was obtained in 76% yield following oxidation. $^1$HNMR (CDCl$_3$) δ4.62 (2H, s), 6.68 (1H, d, $J_{H,H}$=11.92), 7.18–7.60 (8H aromatic+1H ethylenic).

Synthesis Example 44
(Z)-4-chlorostyryl 2-chlorobenzylsulfone

A solution of 4-chlorophenylacetylene (0.02 mol) and 2-chlorobenzyl mercaptan (0.02 mol) and metallic sodium (0.02 g atom) was subjected to Procedure 2 to form (Z)-4-chlorostyryl 2-chlorobenzylsulfide. The title compound was obtained in 73% yield following oxidation. $^1$HNMR (CDCl$_3$) δ4.56 (2H, s), 6.70 (1H, d, $J_{H,H}$=12.05), 7.18–7.64 (8H aromatic+1H ethylenic).

Synthesis Example 45
(Z)-4-chlorostyryl 4-fluorobenzylsulfone

A solution of 4-chlorophenylacetylene (0.02 mol) and 4-fluorobenzyl mercaptan (0.02 mol) and metallic sodium (0.02 g atom) was subjected to Procedure 2 to form (Z)-4-chlorostyryl 4-fluorobenzylsulfide. The title compound was obtained in 82% yield following oxidation. $^1$HNMR (CDCl$_3$) δ4.60 (2H, s), 6.70 (1H, d, $J_{H,H}$=11.78), 7.18–7.60 (8H aromatic+1H ethylenic).

Synthesis Example 46
(Z)-4-fluorostyryl benzylsulfone

A solution of 4-fluorophenylacetylene (0.02 mol) and benzyl mercaptan (0.02 mol) and metallic sodium (0.02 g atom) was subjected to Procedure 2 to form (Z)-4-fluorostyryl benzylsulfide. The title compound was obtained in 76% yield following oxidation. $^1$HNMR (CDCl$_3$) δ4.54 (2H, s), 6.68 (1H, d, $J_{H,H}$=11.94), 7.12–7.58 (9H aromatic+1H ethylenic).

Synthesis Example 47
(Z)-4-fluorostyryl 4-chlorobenzylsulfone

A solution of 4-fluorophenylacetylene (0.02 mol) and 4-chlorobenzyl mercaptan (0.02 mol) and metallic sodium (0.02 g atom) was subjected to Procedure 2 to form (Z)-4-fluorostyryl 4-chlorobenzylsulfide. The title compound was obtained in 82% yield following oxidation. $^1$HNMR (CDCl$_3$) δ4.60 (2H, s), 6.68 (1H, d, $J_{H,H}$=11.84), 7.18–7.60 (8H aromatic+1H ethylenic).

Synthesis Example 48
(Z)-4-fluorostyryl 2-chlorobenzylsulfone

A solution of 4-fluorophenylacetylene (0.02 mol) and 2-chlorobenzyl mercaptan (0.02 mol) and metallic sodium (0.02 g atom) was subjected to Procedure 2 to form (Z)-4-fluorostyryl 2-chlorobenzylsulfide. The title compound was obtained in 74% yield following oxidation. $^1$HNMR (CDCl$_3$) δ4.55 (2H, s), 6.66 (1H, d, $J_{H,H}$=11.94), 7.20–7.65 (8H aromatic+1H ethylenic).

Synthesis Example 49
(Z)-4-fluorostyryl 4-fluorobenzylsulfone

A solution of 4-fluorophenylacetylene (0.02 mol) and 4-fluorobenzyl mercaptan (0.02 mol) and metallic sodium (0.02 g atom) was subjected to Procedure 2 to form (Z)-4-fluorostyryl 4-fluorobenzylsulfide. The title compound was obtained in 78% yield following oxidation. $^1$HNMR (CDCl$_3$) δ4.60 (2H, s), 6.65 (1H, d, $J_{H,H}$=11.83), 7.20–7.65 (8H aromatic+1H ethylenic).

Synthesis Example 50
(Z)-4-bromostyryl benzylsulfone

A solution of 4-bromophenylacetylene (0.02 mol) and benzyl mercaptan (0.02 mol) and metallic sodium (0.02 g atom) was subjected to Procedure 2 to form (Z)-4-bromostyryl benzylsulfide. The title compound was obtained in 80% yield following oxidation. $^1$HNMR (CDCl$_3$) δ4.52 (2H, s), 6.80 (1H, d, $J_{H,H}$=11.98), 7.18–7.59 (9H aromatic+1H ethylenic).

Synthesis Example 51
(Z)-4-bromostyryl 4-chlorobenzylsulfone

A solution of 4-bromophenylacetylene (0.02 mol) and 4-chlorobenzyl mercaptan (0.02 mol) and metallic sodium (0.02 g atom) was subjected to Procedure 2 to form (Z)-4-bromostyryl 4-chlorobenzylsulfide. The title compound was obtained in 87% yield following oxidation. $^1$HNMR (CDCl$_3$) δ4.58 (2H, s), 6.72 (1H, d, $J_{H,H}$=12.08), 7.15–7.68 (8H aromatic+1H ethylenic).

Synthesis Example 52
(Z)-4-bromostyryl 2-chlorobenzylsulfone

A solution of 4-bromophenylacetylene (0.02 mol) and 2-chlorobenzyl mercaptan (0.02 mol) and metallic sodium (0.02 g atom) was subjected to Procedure 2 to form (Z)-4-bromostyryl 2-chlorobenzylsulfide. The title compound was obtained in 84% yield following oxidation. $^1$HNMR (CDCl$_3$) δ4.57 (2H, s), 6.70 (1H, d, $J_{H,H}$=11.58), 7.18–7.58 (8H aromatic+1H ethylenic).

Synthesis Example 53
(Z)-4-bromostyryl 4-fluorobenzylsulfone

A solution of 4-bromophenylacetylene (0.02 mol) and 4-fluorobenzyl mercaptan (0.02 mol) and metallic sodium (0.02 g atom) was subjected to Procedure 2 to from (Z)-4-bromostyryl 4-fluorobenzylsulfide. The title compound was obtained in 78% yield following oxidation. $^1$HNMR (CDCl$_3$) δ4.58 (2H, s), 6.65 (1H, d, $J_{H,H}$=11.78), 7.22–7.67 (8H aromatic+1H ethylenic).

Synthesis Example 54
(Z)-4-methylstyryl benzylsulfone

A solution of 4-methylphenylacetylene (0.02 mol) and benzyl mercaptan (0.02 mol) and metallic sodium (0.02 g atom) was subjected to Procedure 2 to form (Z)-4-methylstyryl benzylsulfide. The title compound was obtained in 70% yield following oxidation. $^1$HNMR (CDCl$_3$) δ2.48 (3H, s), 4.60 (2H, s), 6.68 (1H, d, $J_{H,H}$=11.94), 7.20–7.65 (9H aromatic+1H ethylenic).

Synthesis Example 55
(Z)4-methylstyryl 4-chlorobenzylsulfone

A solution of 4-methylphenylacetylene (0.02 mol) and 4-chlorobenzyl mercaptan (0.02 mol) and metallic sodium (0.02 g atom) was subjected to Procedure 2 to form (Z)-4-methylstyryl 4-chlorobenzylsulfide. The title compound was obtained in 74% yield following oxidation. $^1$HNMR (CDCl$_3$) δ2.46 (3H, s), 4.64 (2H, s), 6.75 (1H, d, $J_{H,H}$=12.21), 7.18–7.57 (9H aromatic+1H ethylenic).

Synthesis Example 56
(Z)-4-methylstyryl 2-chlorobenzylsulfone

A solution of 4-methylphenylacetylene (0.02 mol) and 2-chlorobenzyl mercaptan (0.02 mol) and metallic sodium (0.02 g atom) was subjected to Procedure 2 to form (Z)-4-methylstyryl 2-chlorobenzylsulfide. The title compound was obtained in 76% yield following oxidation. $^1$HNMR (CDCl$_3$) δ2.50 (3H, s), 4.58 (2H, s), 6.80 (1H, d, $J_{H,H}$=11.88), 7.20–7.63 (9H aromatic+1H ethylenic).

Synthesis Example 57

(Z)4-methylstyryl 4-fluorobenzylsulfone

A solution of 4-methylphenylacetylene (0.02 mol) and 4-fluorobenzyl mercaptan (0.02 mol) and metallic sodium (0.02 g atom) was subjected to Procedure 2 to form (Z)4-methylstyryl 4-fluorobenzylsulfide. The title compound was obtained in 69% yield following oxidation. $^1$HNMR (CDCl$_3$) δ2.46 (3H, s), 4.62 (2H, s), 6.78 (1H, d, J$_{H,H}$= 11.98), 7.18–7.59 (9H aromatic+1H ethylenic).

The following additional (E)-α,β unsaturated aryl sulfones listed in Tables 3a and 3b were prepared by reacting the appropriate benzylsulfonyl acetic acid and benzaldehyde or arylaldehyde according to Procedure 1, Part B:

TABLE 3a

| Syn. Ex. | M.P. (° C.) | Yield (%) | Compound |
|---|---|---|---|
| 58 | 134–136 | 55 | (E)-2-nitrostyryl-4-fluorobenzylsulfone |
| 59 | 170–173 | 64 | (E)-3-nitrostyryl-4-fluorobenzylsulfone |
| 60 | 151–152 | 61 | (E)-4-nitrostyryl-4-fluorobenzylsulfone |
| 61 | 96–98 | 54 | (E)-2-trifluoromethylstyryl-4-fluorobenzylsulfone |
| 62 | 117–119 | 55 | (E)-3-trifluoromethylstyryl-4-fluorobenzylsulfone |
| 63 | 125–128 | 73 | (E)-4-trifluoromethylstyryl-4-fluorobenzylsulfone |
| 64 | 108–112 | 52 | (E)-2-trifluoromethyl-4-fluorostyryl-4-fluorobenzylsulfone |
| 65 | 128–132 | 58 | (E)-2-nitrostyryl-4-chlorobenzylsulfone |
| 66 | 156–157 | 60 | (E)-3-nitrostyryl-4-chlorobenzylsulfone |
| 67 | 189–191 | 61 | (E)-4-nitrostyryl-4-chlorobenzylsulfone |
| 68 | 100–101 | 55 | (E)-2-trifluoromethylstyryl-4-chlorobenzylsulfone |
| 69 | 155–157 | 58 | (E)-3-trifluoromethylstyryl-4-chlorobenzylsulfone |
| 70 | 164–166 | 59 | (E)-4-trifluoromethylstyryl-4-chlorobenzylsulfone |
| 71 | 115–117 | 63 | (E)-2-trifluoromethyl-4-fluorostyryl-4-chlorobenzylsulfone |
| 72 | 169–171 | 63 | (E)-3-methyl-4-fluorostyryl-4-chlorobenzylsulfone |
| 73 | 136–138 | 57 | (E)-2-nitrostyryl-2,4-dichlorobenzylsulfone |
| 74 | 136–138 | 57 | (E)-2-trifluoromethyl-4-fluorostyryl-2,4-dichlorobenzylsulfone |
| 75 | 131–132 | 63 | (E)-2-nitrostyryl-4-bromobenzylsulfone |
| 76 | 168–170 | 56 | (E)-3-nitrostyryl-4-bromobenzylsulfone |
| 77 | 205–207 | 67 | (E)-4-nitrostyryl-4-bromobenzylsulfone |
| 78 | 102–104 | 57 | (E)-2-trifluoromethylstyryl-4-bromobenzylsulfone |
| 79 | 160–161 | 55 | (E)-3-trifluoromethylstyryl-4-fluorobenzylsulfone |
| 80 | 174–175 | 62 | (E)-4-trifluoromethylstyryl-4-bromobenzylsulfone |
| 81 | 167–168 | 63 | (E)-2-nitrostyryl-4-cyanobenzylsulfone |
| 82 | 192–193 | 62 | (E)-3-nitrostyryl-4-cyanobenzylsulfone |
| 83 | 219–220 | 66 | (E)-4-nitrostyryl-4-cyanobenzylsulfone |
| 84 | 182–184 | 70 | (E)-4-fluorostyryl-4-methylbenzylsulfone |
| 85 | 191–192 | 70 | (E)-4-bromostyryl-4-methylbenzylsulfone |
| 86 | 128–130 | 51 | (E)-2-nitrostyryl-4-methylbenzylsulfone |
| 87 | 201–203 | 56 | (E)-3-nitrostyryl-4-methylbenzylsulfone |
| 88 | 194–195 | 57 | (E)-4-nitrostyryl-4-methylbenzylsulfone |
| 89 | 148–149 | 60 | (E)-4-fluorostyryl-4-methoxybenzylsulfone |
| 90 | 176–177 | 66 | (E)-4-chlorostyryl-4-methoxybenzylsulfone |
| 91 | 179–181 | 60 | (E)-4-bromostyryl-4-methoxybenzylsulfone |
| 92 | 127–129 | 57 | (E)-2-nitrostyryl-4-methoxybenzylsulfone |
| 93 | 153–155 | 59 | (E)-3-nitrostyryl-4-methoxybenzylsulfone |
| 94 | 179–181 | 56 | (E)-4-nitrostyryl-4-methoxybenzylsulfone |
| 95 | 176–177 | 66 | (E)-4-chlorostyryl-4-nitrobenzylsulfone |
| 96 | 199–200 | 60 | (E)-4-fluorostyryl-4-nitrobenzylsulfone |

TABLE 3b

| | | | |
|---|---|---|---|
| 97 | 133–136 | 80 | (E)-2,3,4,5,6-pentafluorostyryl-4-fluorobenzylsulfone |
| 98 | 146–148 | 82 | (E)-2,3,4,5,6-pentafluorostyryl-4-chlorobenzylsulfone |
| 99 | 163–164 | 85 | (E)-2,3,4,5,6-pentafluorostyryl-4-bromobenzylsulfone |
| 100 | 133–136 | 78 | (E)-4-fluorostyryl-2,3,4,5,6-pentafluorobenzylsulfone |
| 101 | 154–155 | 80 | (E)-4-chlorostyryl-2,3,4,5,6-pentafluorobenzylsulfone |
| 102 | 176–177 | 92 | (E)-4-bromostyryl-2,3,4,5,6-pentafluorobenzylsulfone |
| 103 | 171–173 | 84 | (E)-2,3,4,5,6-pentafluorostyryl-3,4-dichlorobenzylsulfone |
| 104 | 137–139 | 84 | (E)-2,3,4,5,6-pentafluorostyryl-2,3,4,5,6-pentafluorobenzylsulfone |
| 105 | 178–181 | 51 | (E)-2,3,4,5,6-pentafluorostyryl-4-iodobenzylsulfone |
| 106 | 211–212 | 54 | (E)-2-hydroxy-3,5-dinitrostyryl-4-fluorobenzylsulfone |
| 107 | 207–209 | 52 | (E)-2-hydroxy-3,5-dinitrostyryl-4-bromobenzylsulfone |
| 108 | 204–205 | 51 | (E)-2-hydroxy-3,5-dinitrostyryl-4-chlorobenzylsulfone |
| 109 | 212–213 | 56 | (E)-2-hydroxy-3,5-dinitrostyryl-2,4-dichlorobenzylsulfone |
| 110 | 142–144 | 52 | (E)-2,4,6-trimethoxystyryl-4-methoxybenzylsulfone |
| 111 | 160–161 | 52 | (E)-3-methyl-2,4-dimethoxystyryl-4-methoxybenzylsulfone |
| 112 | 138–140 | 54 | (E)-3,4,5-trimethoxystyryl-4-methoxybenzylsulfone |
| 113 | ND | ND | (E)-3,4,5-trimethoxystyryl-2-nitro-4,5-dimethoxybenzylsulfone |
| 114 | ND | ND | (E)-2,4,6-trimethoxystyryl-2-nitro-4,5-dimethoxybenzylsulfone |
| 115 | ND | ND | (E)-3-methyl-2,4-dimethoxystyryl-2-nitro-4,5-dimethoxybenzylsulfone |
| 116 | 128–129 | 72 | (E)-2,3,4-trifluorostyryl-4-fluorobenzylsulfone |
| 117 | 141–142 | 78 | (E)-2,3,4-trifluorostyryl-4-chlorobenzylsulfone |
| 118 | 134–136 | 58 | (E)-2,6-dimethoxy-4-hydroxystyryl-4-methoxybenzylsulfone |
| 119 | 154–156 | 56 | (E)-2,3,5,6-tetrafluorostyryl-4-methoxybenzylsulfone |
| 120 | 146–148 | 66 | (E)-2,4,5-trimethoxystyryl-4-methoxybenzylsulfone |
| 121 | 154–156 | 52 | (E)-2,3,4-trimethoxystyryl-4-methoxybenzylsulfone |
| 122 | 203–205 | 56 | (E)-3-nitro-4-hydroxy-5-methoxystyryl-4-methoxybenzylsulfone |
| 123 | 139–141 | 54 | (E)-3,4-dimethoxy-6-nitrostyryl-4-methoxybenzylsulfone |
| 124 | 160–161 | 58 | (E)-3,4-dimethoxy-5-iodostyryl-4-methoxybenzylsulfone |
| 125 | 146–148 | 55 | (E)-2,6-dimethoxy-4-fluorostyryl-4-methoxybenzylsulfone |
| 126 | ND | ND | (E)-2-hydroxy-4,6-dimethoxystyryl-4-methoxybenzylsulfone |
| 127 | 97–99 | 51 | (E)-2,4,6-trimethylstyryl-4-methoxybenzylsulfone |
| 128 | 181–183 | 54 | (E)-2,4,6-trimethoxystyryl-4-chlorobenzylsulfone |
| 129 | 119–121 | 55 | (E)-2,6-dimethoxy-4-fluorostyryl-4-chlorobenzylsulfone |
| 130 | ND | ND | (E)-2-hydroxy-4,6-dimethoxystyryl-4-chlorobenzylsulfone |
| 131 | 178–181 | 54 | (E)-2,4,6-trimethoxystyryl-4-bromobenzylsulfone |
| 132 | 116–118 | 58 | (E)-2,6-dimethoxy-4-fluorostyryl-4-bromobenzylsulfone |
| 133 | 94–96 | 52 | (E)-2,4,6-trimethoxystyryl-2,3,4-trimethoxybenzylsulfone |
| 134 | 110–112 | 54 | (E)-2,6-dimethoxystyryl-2,3,4-trimethoxybenzylsulfone |
| 135 | 151–153 | 54 | (E)-2,4,6-trimethoxystyryl-,3,4,5-trimethoxybenzylsulfone |

TABLE 3b-continued

| 136 | 146–149 | 53 | (E)-2,6-dimethoxystyryl-3,4,5-trimethoxybenzylsulfone |
| 137 | 96–99 | 68 | (E)-4-fluorostyryl-2,3,4-trimethoxybenzylsulfone |

ND = Not determined.

Examples of further (E)-α,β unsaturated aryl sulfone compounds according to formula 1a, below, are provided in Table 4. In each compound, one of $Q_1$ or $Q_2$ is other than phenyl or substituted phenyl. Each compound was prepared by reacting the appropriate benzylsulfonyl acetic acid or (aryl)methyl sulfonyl acetic acid with the appropriate benzaldehyde or arylaldehyde according to Procedure 1, Part B. 3-Thiophene-1,1-dioxoethenyl compounds were prepared from the corresponding 3-thiopheneethenyl compound by refluxing a solution of the 3-thiopheneethenyl compound in glacial acetic acid (10 ml) and 30% hydrogen peroxide (1 ml) for 1 hour, followed by pouring the cooled contents onto crushed ice (100 g). The solid material separated was filtered and recrystallized from 2-propanol.

TABLE 4

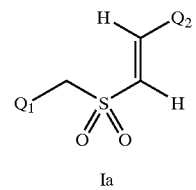

Ia

| Syn. Ex. | M.P. (° C.) | % Yield | $Q_1$ | $Q_2$ |
|---|---|---|---|---|
| 138 | 110–111 | 54 | 4-fluorophenyl | 2-pyridyl |
| 139 | 155–156 | 60 | 4-fluorophenyl | 3-pyridyl |
| 140 | ND | 52 | 4-fluorophenyl | 4-pyridyl |
| 141 | 117–119 | 53 | 4-chlorophenyl | 2-pyridyl |
| 142 | 167–169 | 51 | 4-chlorophenyl | 3-pyridyl |
| 143 | 107–109 | 53 | 4-chlorophenyl | 4-pyridyl |
| 144 | 143–145 | 52 | 4-bromophenyl | 2-pyridyl |
| 145 | 161–162 | 59 | 4-bromophenyl | 3-pyridyl |
| 146 | 158–160 | 54 | 4-bromophenyl | 4-pyridyl |
| 147 | 146–148 | 53 | 4-fluorophenyl | 2-thienyl |
| 149 | 158–159 | 56 | 4-chlorophenyl | 2-thienyl |
| 149 | 169–170 | 54 | 4-bromophenyl | 2-thienyl |
| 150 | 155–157 | 54 | 4-fluorophenyl | 4-bromo-2-thienyl |
| 151 | 150–151 | 53 | 4-chlorophenyl | 4-bromo-2-thienyl |
| 152 | 154–155 | 54 | 4-bromophenyl | 4-bromo-2-thienyl |
| 153 | 161–162 | 55 | 4-fluorophenyl | 5-bromo-2-thienyl |
| 154 | 190–192 | 50 | 4-chlorophenyl | 5-bromo-2-thienyl |
| 155 | 199–200 | 52 | 4-bromophenyl | 5-bromo-2-thienyl |
| 156 | 126–128 | 52 | 4-fluorophenyl | 2-thienyl-1,1-dioxide |
| 157 | 108–110 | 55 | 4-chlorophenyl | 2-thienyl-1,1-dioxide |
| 158 | 145–147 | 56 | 4-bromophenyl | 2-thienyl-1,1-dioxide |
| 159 | 159–161 | 53 | 4-fluorophenyl | 3-thienyl |
| 160 | 169–170 | 59 | 4-chlorophenyl | 3-thienyl |
| 161 | 175–177 | 70 | 4-bromophenyl | 3-thienyl |
| 162 | 177–179 | 52 | 4-iodophenyl | 3-thienyl |
| 163 | 135–136 | 55 | 4-methylphenyl | 3-thienyl |
| 164 | 130–131 | 55 | 4-methoxyphenyl | 3-thienyl |
| 165 | 201–202 | 52 | 4-trifluoro-methylphenyl | 3-thienyl |
| 166 | 125–126 | 53 | 2,4-dichlorophenyl | 3-thienyl |
| 167 | 152–153 | 51 | 3,4-dichlorophenyl | 3-thienyl |
| 168 | 168–170 | 54 | 4-cyanophenyl | 3-thienyl |
| 169 | 203–205 | 54 | 4-nitrophenyl | 3-thienyl |
| 170 | 95–99 | 52 | 4-fluorophenyl | 3-thienyl-1,1-dioxide |
| 171 | 115–120 | 51 | 4-chlorophenyl | 3-thienyl-1,1-dioxide |
| 172 | 152–155 | 50 | 4-bromophenyl | 3-thienyl-1,1-dioxide |
| 173 | 92–95 | 54 | 4-methoxyphenyl | 3-thienyl-1,1-dioxide |
| 174 | 135–139 | 52 | 2,4-dichlorophenyl | 3-thienyl-1,1-dioxide |
| 175 | 103–105 | 53 | 4-fluorophenyl | 2-furyl |
| 176 | 106–108 | 52 | 4-chlorophenyl | 2-furyl |
| 177 | 125–127 | 52 | 4-bromophenyl | 2-furyl |
| 178 | 114–117 | 51 | 4-fluorophenyl | 3-furyl |
| 179 | 154–156 | 50 | 4-chlorophenyl | 3-furyl |
| 180 | 156–158 | 51 | 4-bromophenyl | 3-furyl |
| 181 | 166–170 | 52 | 4-iodophenyl | 3-furyl |
| 182 | 123–126 | 53 | 4-methylphenyl | 3-furyl |
| 183 | 117–119 | 51 | 4-methoxyphenyl | 3-furyl |
| 184 | 167–169 | 51 | 4-trifluoro-methylphenyl | 3-furyl |
| 185 | 104–106 | 53 | 2,4-dichlorophenyl | 3-furyl |
| 186 | 131–133 | 52 | 3,4-dichlorophenyl | 3-furyl |
| 187 | 175–178 | 53 | 4-cyanophenyl | 3-furyl |
| 188 | 210–213 | 52 | 4-nitrophenyl | 3-furyl |
| 189 | 133–137 | 51 | 4-chlorophenyl | 2-thiazolyl |

TABLE 4-continued

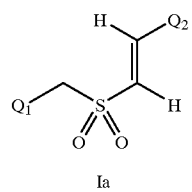

Ia

| Syn. Ex. | M.P. (° C.) | % Yield | Q₁ | Q₂ |
|---|---|---|---|---|
| 190 | ND | ND | 4-chlorophenyl | 2-pyrrolyl |
| 191 | ND | ND | 4-bromophenyl | 2-pyrrolyl |
| 192 | 228–230 | 56 | 4-chlorophenyl | 2-nitro-4-thienyl |
| 193 | 177–179 | 67 | 4-iodophenyl | 2-nitro-4-thienyl |
| 194 | 228–230 | 64 | 2,4-dichlorophenyl | 2-nitro-4-thienyl |
| 195 | 170–172 | 56 | 4-methoxyphenyl | 2-nitro-4-thienyl |
| 196 | 148–150 | 55 | 4-fluorophenyl | 1-naphthyl |
| 197 | 185–186 | 58 | 4-fluorophenyl | 2-naphthyl |
| 198 | 142–143 | 63 | 4-chlorophenyl | 1-naphthyl |
| 199 | 191–193 | 52 | 4-chlorophenyl | 2-naphthyl |
| 200 | 147–149 | 52 | 4-bromophenyl | 1-naphthyl |
| 201 | 193–194 | 54 | 4-bromophenyl | 2-naphthyl |
| 202 | 142–144 | 52 | 1-naphthyl | 4-fluorophenyl |
| 203 | 195–197 | 53 | 1-naphthyl | 4-chlorophenyl |
| 204 | 207–209 | 55 | 1-naphthyl | 4-bromophenyl |
| 205 | 188–192 | 62 | 1-naphthyl | 2-nitrophenyl |
| 206 | 192–194 | 59 | 1-naphthyl | 3-nitrophenyl |
| 207 | 252–254 | 61 | 1-naphthyl | 4-nitrophenyl |
| 208 | 93–95 | 56 | 4-fluorophenyl | 9-anthryl |
| 209 | 122–124 | 53 | 4-chlorophenyl | 9-anthryl |
| 210 | 172–175 | 51 | 4-bromophenyl | 9-anthryl |

Synthesis Examples 211–213 exemplify the preparation of (E)(Z)-bis(styryl)sulfones. Synthesis Examples 214–219 exemplify the preparation of 2-(phenylsulfonyl)-1-phenyl-3-phenyl-2-propen-1-ones.

Synthesis Example 211
(Z)-styryl-(E)-4-fluorostyryl sulfone

A solution of (Z)-styryl sulfonylacetic acid (0.01 mol) and 4-fluorobenzaldehyde (0.01 mol was subjected to Procedure 3. The title compound was obtained in 68% yield.

Synthesis Example 212
(Z)-styryl-(E)-4-bromostyryl sulfone

A solution of (Z)-styryl sulfonylacetic acid (0.01 mol) and 4-bromobenzaldehyde (0.01 mol) was subjected to Procedure 3. The title compound was obtained in 70% yield.

Synthesis Example 213
(Z)-styryl-(E)-4-chlorostyryl sulfone

A solution of (Z)-styryl sulfonylacetic acid (0.01 mol) and 4-chlorobenzaldehyde (0.01 mol) was subjected to Procedure 3. The title compound was obtained in 64% yield.

Synthesis Example 214
2-[(4-fluorophenyl)sulfonyl]-1-phenyl-3-(4-fluorophenyl)-2-propen-1-one A solution of phenacyl-4-fluorophenyl sulfone (0.01 mol) and 4-fluorobenzaldehyde (0.01 mol) was subjected to Method 1 of Procedure 4. The title compound was obtained in 63% yield.

Synthesis Example 215
2-[(2-chlorophenyl)-sulfonyl]-1-phenyl-3-(4-fluorophenyl)-2-propen-1-one A solution of phenacyl-2-chlorophenyl sulfone (0.01 mol) and 4-fluorobenzaldehyde (0.01 mol) was subjected to Method 1 of Procedure 4. The title compound was obtained in 58% yield.

Synthesis Example 216
2-[(2-chlorophenyl)sulfonyl]-1-phenyl-3-(4-bromophenyl)-2-propen-1-one A solution of phenacyl-2-chlorophenyl sulfone (0.01 mol) and 4-bromobenzaldehyde (0.01 mol) was subjected to Method 1 of Procedure 4. The title compound was obtained in 66% yield.

Synthesis Example 217
2-[(4-chlorophenyl)sulfonyl]-1-phenyl-3-(4-bromophenyl)-2-propen-1-one A solution of phenacyl-4-chlorophenyl sulfone (0.01 mol) and 4-bromobenzaldehyde (0.01 mol) was subjected to Method 1 of Procedure 4. The title compound was obtained in 60% yield.

Synthesis Example 218
2-[(2-nitrophenyl)sulfonyl]-1-phenyl-3-(4-bromophenyl)-2-propen-1-one A solution of phenacyl-2-nitrophenyl sulfone (0.01 mol) and 4-bromobenzaldehyde (0.01 mol) was subjected to Method 1 of Procedure 4. The title compound was obtained in 56% yield.

Synthesis Example 219
2-(phenylsulfonyl)-1-phenyl-3-(4-fluorophenyl)-2-propen-1-one A solution of phenacylphenyl sulfone (0.01 mol) and 4-fluorobenzaldehyde (0.01 mol) was subjected to Method 1 of Procedure 4. The title compound, melting point 142–143° C., was obtained in 62% yield.

Infrared and nuclear magnetic resonance spectroscopy analyses of the compounds of Synthesis Examples 211 through 218 are set forth in Table 5:

TABLE 5

| | IR and NMR Spectroscopy | | |
|---|---|---|---|
| 211 | — | 1300, 1120 | 6.55(1H, d, $J_{H,H}$=10.8), 6.70(1H, d, $J_{H,H}$=14.8), 7.20–7.92(m, 9H aromatic, 2H vinyl) |
| 212 | — | 1318, 1128 | 6.68(1H, d, $J_{H,H}$=11.0), 6.86(1H, d, $J_{H,H}$=15.0), 7.15–7.90(m, 9H aromatic, 2H vinyl) |
| 213 | — | 1330, 1100 | 6.65(1H, d, $J_{H,H}$=11.2), 6.81(1H, d, $J_{H,H}$=15.4), 7.00–7.85(m, 9H aromatic, 2H vinyl) |
| 214 | 1620 | 1320, 1145 | 8.04(1H, s, —C=CH) 7.35–7.95(m, 13H) |
| 215 | 1625 | 1320, 1148 | 8.48(1H, s, —C=CH) 7.40–8.25(m, 13H) |
| 216 | 1618 | 1315, 1140 | 8.05(1H, s, —C=CH) 7.28–8.00(m, 13H) |
| 217 | 1620 | 1318, 1142 | 8.47(1H, s, —C=CH) 7.30–8.15(m, 13H) |
| 218 | 1618 | 1315, 1140 | 8.57(1H, s, —C=CH) 7.40–8.20(m, 13H) |

EXAMPLE 1

Plating Efficiency of Normal vs. Cancer Cells in the Presence of (E)-4-Fluorostyryl-4-Chlorobenzylsulfone HFL-1 cells (normal, human diploid lung fibroblasts) purchased from ATCC were plated after first passage at low density ($2.0 \times 10^5$ cells) per well (6 well dishes) in one ml of growth medium (DMEM completed with 10% fetal bovine serum and pen/strep). Twenty-four hours later, (E)-4-fluorostyryl-4-chlorobenzylsulfone was added to each well at the following final concentrations; 0 μM, 2.5 μM, 5.0 μM, 25 μM, 50 μM, and 75 μM. After a 24 hour incubation period, the wells were washed 3× with 5 ml normal growth medium and each well was trypsinized and cell counts were determined. To determine colony-forming ability, the cells from each treatment were then serial diluted and replated into 100 mm dishes such that each group was split into 3 replating groups consisting of 10, 100, 200 cells per plate. The groups were plated in triplicate. The cells were incubated for 20 days under normal growth conditions and colonies were counted after staining with modified Wright stain (Sigma). The number of colonies from each plate in triplicate were determined and the average for each group was plotted. The results are set forth in FIG. 1. The concentration of the drug causing 50% inhibition in plating efficiency was calculated and found to be 70 μM.

EXAMPLE 2

Figure 2:
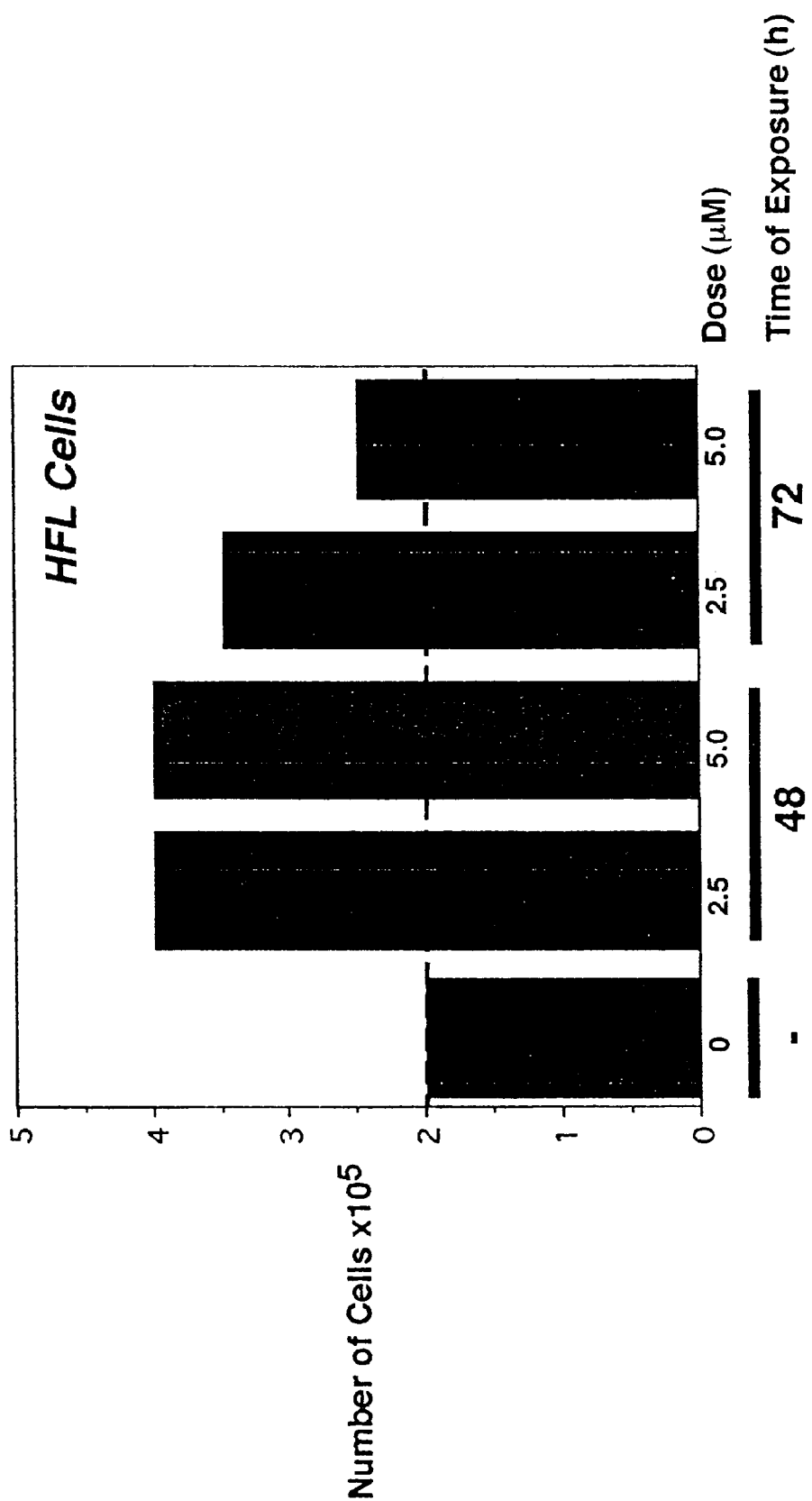
FIG. 2 shows the effect of long term exposure of HFL-1 to (E)-4-fluorostyryl-4-chlorobenzylsulfone. Cells were exposed to either 2.5 or 5.0 $\mu$M of the styryl sulfone for 96 hours and counted.

Effect of Long Term Exposure of Normal Human Fibroblasts to (E)-4-Fluorostyryl-4-Chlorobenzylsulfone HFL-1 cells were plated at a cell density of $1.0 \times 10^5$ per well 24 hours prior to drug addition. Cells were exposed to either 2.5 or 5.0 μM (E)-4-fluorostyryl-4-chlorobenzylsulfone for 48 or 72 hours. Cells were counted 96 hours after the incubation period. The results are shown in FIG. 2. The cells exhibited transiently reduced replication rates.

EXAMPLE 3

Figure 3:
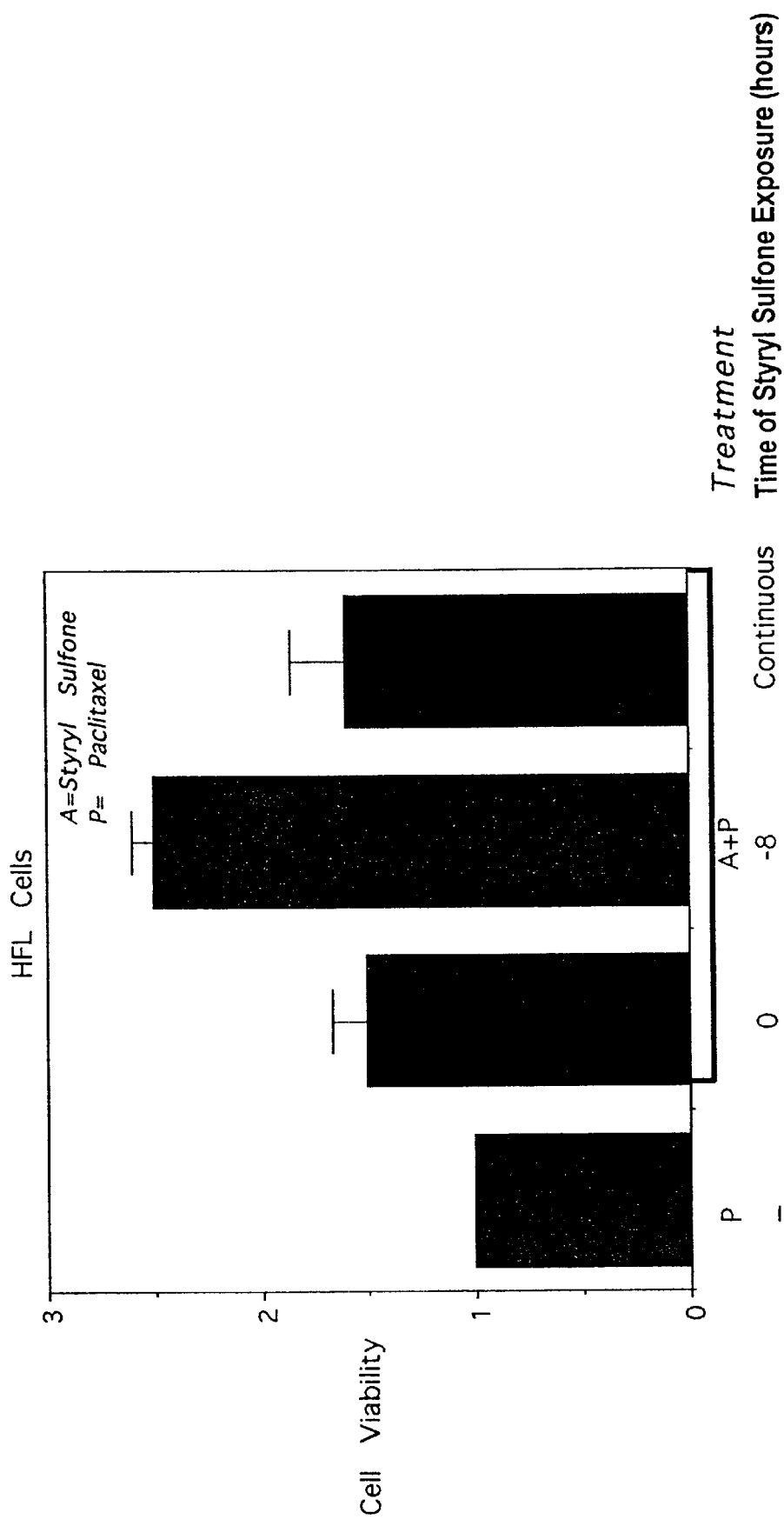
FIG. 3 is a graph of the effect of paclitaxel on HFL-1 cells which were either pre-treated with (E)-4-fluorostyryl-4-chlorobenzylsulfone and then exposed to paclitaxel, or treated simultaneously with both agents. Cells were enumerated 96 hours after exposure to paclitaxel.

(E)4-Fluorostyryl-4-Chlorobenzylsulfone Protection of Normal Human Fibroblasts from Paclitaxel Cytotoxicity HFL-1 cells were plated at a cell density of $1.0 \times 10^5$ per well 24 hours prior to drug addition. Cells were pretreated with (E)-4-fluorostyryl-4-chlorobenzylsulfone (2.0 μM) for 8 hours and then exposed to paclitaxel (250 μM). Other cells were treated with paclitaxel alone, or both agents simultaneously. Cells were enumerated by Trypan blue exclusion using a hematocytometer 96 hours after exposure to paclitaxel. The results are shown in FIG. 3. The ordinate in FIG. 3 represents the number of viable cells following treatment with (E)-4-fluorostyryl-4-chlorobenzylsulfone and paclitaxel, divided by the number of viable cells remaining after treatment with paclitaxel alone. Pretreatment with (E)-4-fluorostyryl-4-chlorobenzylsulfone conferred protection from the toxic effects of paclitaxel.

EXAMPLE 4

(E)-4-Fluorostyryl-4-Chlorobenzylsulfone Protection of Normal Human Fibroblasts from Anticancer Agent Cytotoxicity HFL-1 cells were plated at a cell density of $1.0 \times 10^5$ in 1 ml of medium. Twenty-four hours following plating, 2.0 μM of (E)-4-fluorostyryl-4-chlorobenzylsulfone was added to the medium. Following a 24 hour preincubation with the styryl sulfone, the various cytotoxic agents listed in Table 6 were added to the cells, at the concentrations given in Table 6. the number of viable cells was determined by Trypan blue exclusion using a hematocytometer 96 hours after exposure to cytotoxic agent. The results appear in Table 6. The "Protection Ratio" is the number of viable cells following treatment with (E)-4-fluorostyryl-4-chlorobenzylsulfone and cytotoxic agent, divided by the number of viable cells remaining after treatment with cytotoxic agent alone. A protection ratio of 2 or more is considered highly significant, while is protection ratio of 1.5–2 is considered less significant. As shown in Table 6, normal cells were protected by the styryl sulfone from the cytotoxic effect of mitotic phase cell cycle inhibitors and topoisomerase inhibitors, but not from the cytotoxic effect of drugs of other classes.

TABLE 6

Protective Effect of (E)-4-Fluorostyryl-4-Chlorobenzylsulfone on HFL-1 Cells Treated with Cytotoxic Drugs

| Cytotoxic Drug | | | |
|---|---|---|---|
| name | conc. μM | Drug Class | Protection Ratio |
| paclitaxel | 0.25 | antimitotic | 2.5 |
| vincristine | 0.25 | antimitotic | 3.0 |
| camptothecin | 0.5 | topoisomerase I inhibitor | 2.1 |
| etoposide | 3.0 | topoisomerase II inhibitor | 3.5 |
| mitoxantrone | 0.3 | topoisomerase II inhibitor | 2.0 |
| doxorubicin | 0.4 | topoisomerase II inhibitor | 1.5 |
| 5-fluorouracil | 20 | DNA antimetabolite | 1.3 |
| cisplatin | 5.0 | alkylating agent | 1.3 |

EXAMPLE 5

Figure 4:
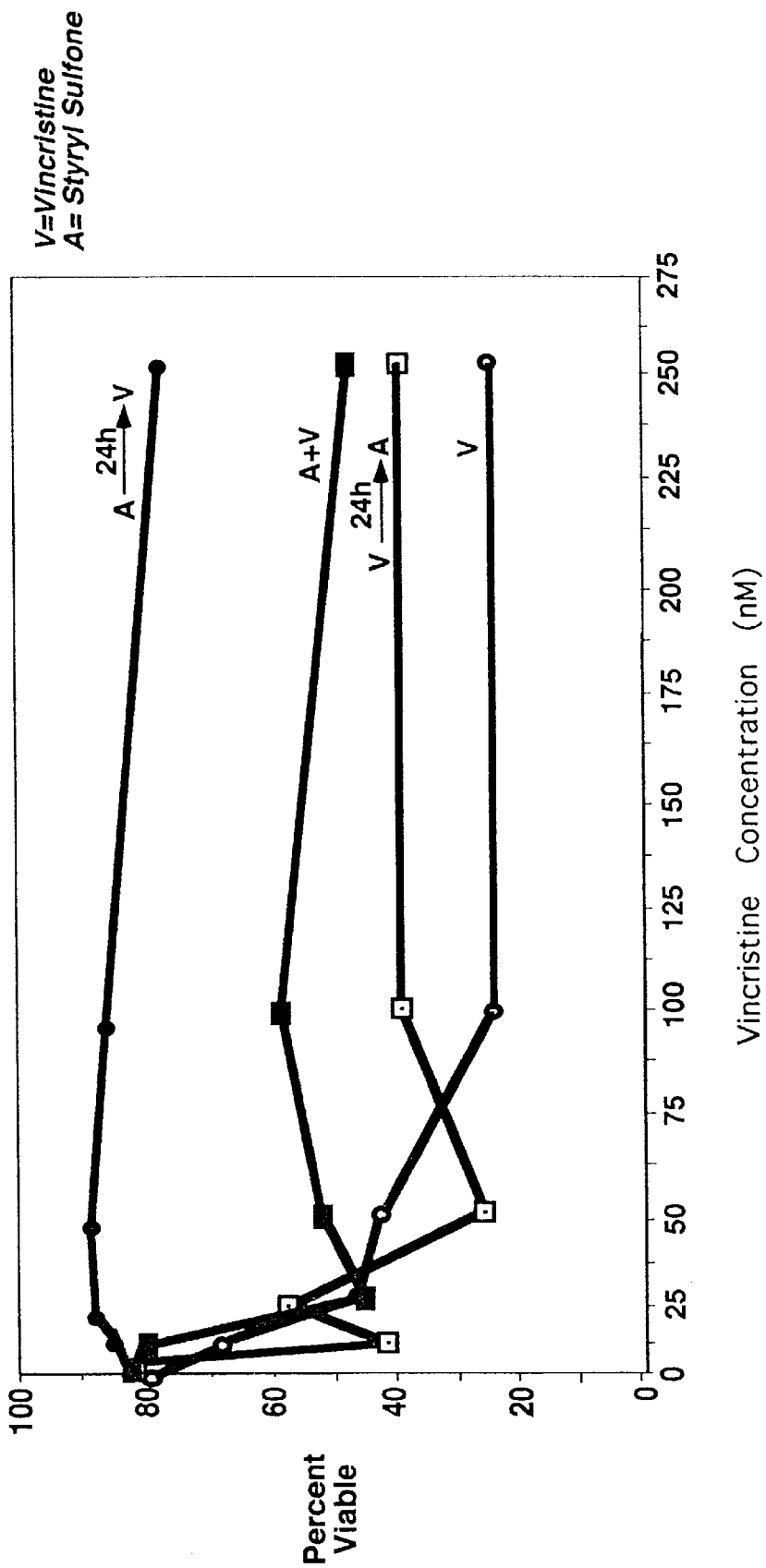
FIG. 4 is a plot of the effect of vincristine on HFL-1 cells Vincristine toxicity is abrogated by styryl sulfone treatment. Normal HFL cells were treated with 0 to 0.250 nM vincristine and 2.0 $\mu$M (E)-4-fluorostyryl-4-chlorobenzylsulfone as indicated. Cell viability was assessed 96 hours after vincristine was added. "V", vincristine alone; "A→V", styryl sulfone followed by vincristine 24 hours later; "A+V", simultaneous styryl sulfone and vincristine treatment; "V→A", vincristine followed by styryl sulfone 24 hours later.

(E)-4-Fluorostyryl-4-Chlorobenzylsulfone Protection of Normal Human Fibroblasts from Vincristine Cytotoxicity HFL-1 cells were treated with 0–250 mM vincristine and, optionally, 2.0 μM (E)-4-fluorostyryl-4-chlorobenzylsulfone either 24 hours before or after vincristine treatment, or simultaneously with vincristine treatment. Cell viability was assessed 96 hours after the addition of vincristine. The results are shown in FIG. 4: "V", vincristine alone; "A→V", styryl sulfone followed by vincristine 24 hours later; "A+V", simultaneous styryl sulfone and vincristine treatment; "V→A", vincristine followed by styryl sulfone 24 hours later. Pretreatment with(E)-4-fluorostyryl-4-chlorobenzylsulfone conferred protection from the toxic effects of vincristine.

EXAMPLE 6

Figure 5:
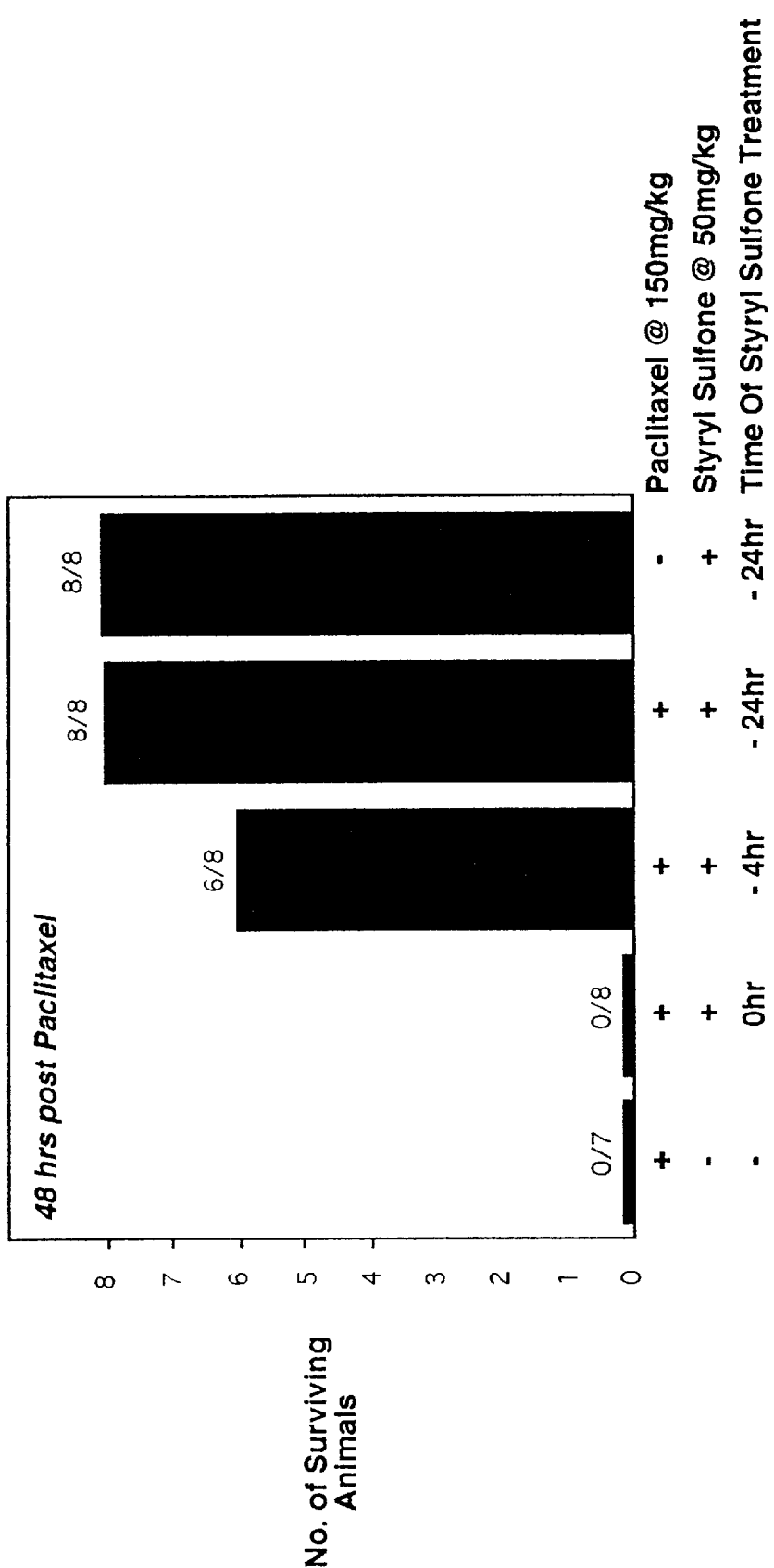
FIG. 5 shows the effect of the styryl sulfone (E)-4-fluorostyryl-4-chlorobenzylsulfone in protecting mice from paclitaxel cytotoxicity. The styryl sulfone was given 24 hours before paclitaxel, 4 hours before paclitaxel, or simultaneously with paclitaxel. Control animals received paclitaxel alone or styryl sulfone alone. Mortality was assessed 48 after paclitaxel injection.
Figure 6:
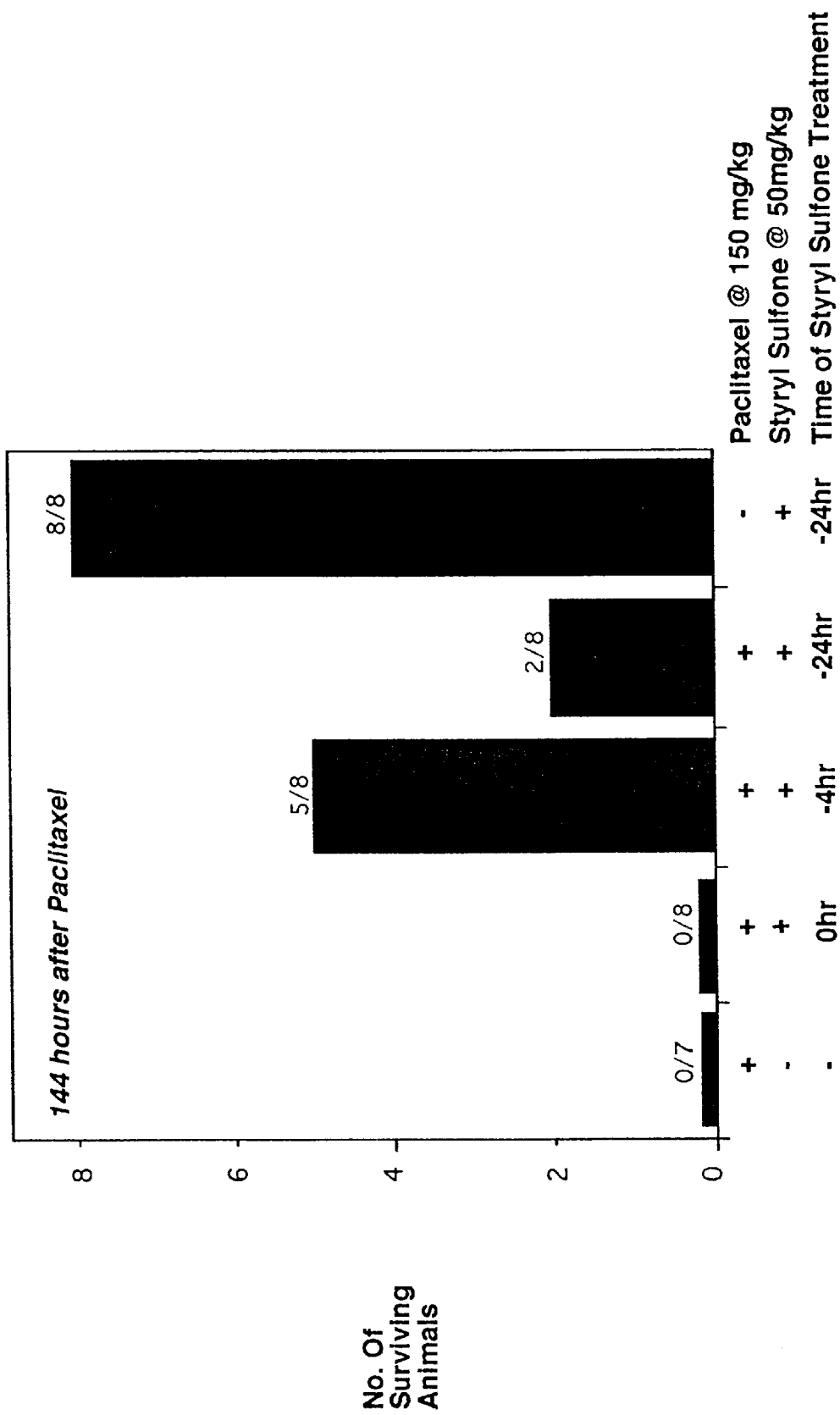
FIG. 6 is similar to FIG. 5, except that mortality was assessed 144 hours post paclitaxel administration.

(E)-4-Fluorostyryl-4-Chlorobenzylsulfone Protection of Mice from Paclitaxel Toxicity ICR female mice age 10–12 weeks (Taconic) were divided into the following treatment groups and received intraperitoneal injections of 50 mg/Kg (E)-4-fluorostyryl-4-chlorobenzylsulfone dissolved in DMSO and/or 150 mg/kg paclitaxel (Taxol, Sigma Chemical Co.) dissolved in DMSO. The styryl sulfone was given 24 hours before paclitaxel, 4 hours before paclitaxel, or simultaneously with paclitaxel. Control animals received paclitaxel alone or styryl sulfone alone. Mortality was assessed 48 and 144 hours after paclitaxel injection. The results are shown in FIG. 5 (48 hours post paclitaxel administration) and FIG. 6 (144 hours post paclitaxel administration). Paclitaxel toxicity in mice is abrogated by pre-treatment with (E)-4-fluorostyryl-4-chlorobenzylsulfone.

EXAMPLE 7–12

Antitumor and Cytoprotection Assay of Styryl Sulfones

A. Antitumor Assay

The styryl benzylsulfones listed in Table 7, below were tested for antitumor activity as follows. A panel of the following human carcinoma cell lines was plated at a cell density of $1.0 \times 10^5$ cells per well in six culture plates: prostate tumor cell line DU-145; breast tumor cell line MCF-7; non-small cell lung carcinoma cell line H157; and colorectal carcinoma cell line DLD-1. The compounds were added to the cultures at a final concentration of 2.5 µM, and 96 hours later the total number of viable cells was determined by counting the number of viable cells, as determined by Trypan blue exclusion, using a hematocytometer. The activity of each compound was determined by comparing the viable cell number of treated to untreated controls. The results appear in Table 7.

B. Cytoprotection Assay

The cytoprotective activity of the same lstyryl benzylsulfones was determined as follows. Normal human HFL-1 cells were plated at a cell density of $1.0 \times 10^5$ cells per well in six culture plates. Styryl benzylsulfone was added 24 hours later at a final concentration of either 2.0 or 10 µM. The time of styryl sulfone addition was designated as time zero. Paclitaxel (250 nM) was added at either time zero, or 24 hours after time zero. The total number of viable cells was determined, as described above, after 96 hours of paclitaxel treatment. A compound was deemed to be active if the number of viable cells following the combination treatment was higher than the number of cells after treatment with paclitaxel alone. The data are set forth in Table 7.

TABLE 7

Antitumor and Cytoprotective Effect of Styryl Sulfones

| Ex. | Compound | Anti-tumor | Cyto-protection |
|---|---|---|---|
| 7 | (E)-4-fluorostyryl-4-chlorobenzyl sulfone | + | + |
| 8 | (E)-4-chlorostyryl-4-chlorobenzyl sulfone | + | + |
| 9 | (E)-2-chloro-4-fluorostyryl-4-chlorobenzyl sulfone | + | + |
| 10 | (E)-4-carboxystyryl-4-chlorobenzyl sulfone | − | + |
| 11 | (E)-4-fluorostyryl-2,4-dichlorobenzyl sulfone | + | + |
| 12 | 2-(phenylsulfonyl)-1-phenyl-3-(4-fluorophenyl)-2-propen-1-one | − | + |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. (E)-4-carboxystyryl-4-chlorobenzyl sulfone, or pharmaceutically acceptable salt thereof.

2. A composition comprising:
    (E)-4-carboxystyryl-4-chlorobenzyl sulfone, or pharmaceutically acceptable salt thereof; and
    a pharmaceutically acceptable carrier.

* * * * *